United States Patent
Van De Sande et al.

(10) Patent No.: US 10,748,226 B2
(45) Date of Patent: Aug. 18, 2020

(54) METHOD OF GENERATING, STORING AND MINING DATA RELATED TO KEY OPINION LEADERS IN SCIENTIFIC FIELDS AND COMPUTER SYSTEM CONFIGURED FOR PRESENTING AN EXPLORABLE GRAPHICAL USER INTERFACE

(71) Applicant: UCB BIOPHARMA SRL, Brussels (BE)

(72) Inventors: Bram Van De Sande, Brussels (BE); Arnaud Lieutenant, Brussels (BE)

(73) Assignee: UCB BIOPHARMA SRL, Brussels (BE)

(*) Notice: Subject to any disclaimer, the term of this patent is extended or adjusted under 35 U.S.C. 154(b) by 712 days.

(21) Appl. No.: 15/258,645

(22) Filed: Sep. 7, 2016

(65) Prior Publication Data
US 2018/0068406 A1 Mar. 8, 2018

(51) Int. Cl.
*G16H 70/40* (2018.01)
*G16H 10/20* (2018.01)
(Continued)

(52) U.S. Cl.
CPC ............ *G06Q 50/22* (2013.01); *G06F 16/22* (2019.01); *G06F 16/2465* (2019.01);
(Continued)

(58) Field of Classification Search
CPC .......................... G06F 2216/03; G16H 70/00
See application file for complete search history.

(56) References Cited

U.S. PATENT DOCUMENTS 9,262,514 B2    2/2016   Eckardt et al.
2004/0073476 A1 4/2004   Donahue et al.
(Continued)

FOREIGN PATENT DOCUMENTS

WO    WO2011031790    3/2011

OTHER PUBLICATIONS

PCT Search Report and Written Opinion for corresponding PCT application.
(Continued)

*Primary Examiner* — Sheetal R Paulson
(74) *Attorney, Agent, or Firm* — Davidson, Davidson & Kappel, LLC

(57) ABSTRACT

A method of storing and ingesting data related to key opinion leaders is provided. The method includes extracting published works data, individual data, organization data and subject matter data for a plurality of published scientific works to identify entities for each of the published scientific works and storing the published works data, the individual data, the organization data and the subject matter data in a graph database as an explorable network in which each of the entities is represented by a respective node, the published scientific works including at least one of results of clinical trials and biomedical scientific publications, the entities including the published scientific works, individuals, organizations and subjects, the nodes including published work nodes representing the published scientific works, individual nodes representing the individuals, organization nodes representing the organizations and subject matter nodes representing the subjects, each of the individual nodes being linked to at least one of the other individual nodes, at least one of the organization nodes and at least one of the subject matter nodes, the graph database being configured such that the individual nodes, organization nodes and subject nodes
(Continued)

are each displayable on a graphical user interface as a center node icon in a partial view of the explorable network with linked nodes being generated as outer node icons surrounding the center node icon. The method also includes mining the explorable network stored in the graph database to augment the explorable network with supplemental information for each individual in the explorable network. The supplemental information is relevant to each individual being a key opinion leader. The method also includes storing the supplemental information for each individual in the explorable network such that upon selection of a node icon representing one or more of the individual nodes the corresponding supplemental information for the one or more individuals represented by the one or more individual nodes is generated on the graphical user interface.

26 Claims, 22 Drawing Sheets

(51) Int. Cl.

| | | |
|---|---|---|
| *G16H 70/60* | (2018.01) | |
| *G16H 70/00* | (2018.01) | |
| *G06Q 50/22* | (2018.01) | |
| *G06F 16/22* | (2019.01) | |
| *G06F 16/25* | (2019.01) | |
| *G06F 16/2458* | (2019.01) | |
| *G06F 16/901* | (2019.01) | |
| *G06F 19/00* | (2018.01) | |
| *G06Q 30/02* | (2012.01) | |

(52) U.S. Cl.
CPC .......... *G06F 16/25* (2019.01); *G06F 16/9024* (2019.01); *G06F 19/324* (2013.01); *G06Q 30/0201* (2013.01); *G16H 10/20* (2018.01); *G16H 70/00* (2018.01); *G16H 70/40* (2018.01); *G16H 70/60* (2018.01); *G06F 2216/03* (2013.01)

(56) References Cited

U.S. PATENT DOCUMENTS

| | | |
|---|---|---|
| 2006/0106847 A1* | 5/2006 | Eckardt, III ........ G06F 16/3323 |
| 2007/0067210 A1 | 3/2007 | Rishell et al. |
| 2011/0066714 A1 | 3/2011 | Topham et al. |
| 2013/0138478 A1 | 5/2013 | Hyde et al. |
| 2015/0254289 A1 | 9/2015 | Junkergard et al. |

OTHER PUBLICATIONS

Sharara et al., "Active Surveying: A Probabilistic Approach for Identifying Key Opinion Leaders," Proceedings of the Twenty-Second International Joint Conference on Artificial Intelligence, 2011.

Taylor et al., poster entitled "Identification of Emerging Key Opinion Leaders Using Bibliometric Data Analysis," 2015, accessed at http://pharmafellows.rutgers.edu/resources/7d4b6e9178de4393af9be683240231d4.pdf on Sep. 7, 2016.

Genpact, "Key Opinion Leader Management," 2012, accessed at http://www.genpact.com/downloadable-content/insight/key-opinion-leader-management.pdf on Sep. 7, 2016.

Lynx Research, "Finding Key Opinion Leaders: Using Large Scale Social Network Analysis," 2007, accessed at http://www.lnxpharma.com/Whitepapers/Lnx_Whitepaper_2.pdf on Sep. 7, 2016.

* cited by examiner

METHOD OF GENERATING, STORING AND MINING DATA RELATED TO KEY OPINION LEADERS IN SCIENTIFIC FIELDS AND COMPUTER SYSTEM CONFIGURED FOR PRESENTING AN EXPLORABLE GRAPHICAL USER INTERFACE

The present disclosure relates generally to key opinion leader exploration and more specifically to a method and system for generating an explorable key opinion leader graphical user interface for identifying key opinion leaders in scientific fields.

BACKGROUND

Key opinion leaders ("KOLs") are experts and advisors that have earned a reputation in their field. They are an important resource to organizations, providing in-depth information and counsel on trends and activities within specific knowledge areas. In the medical field, KOLs are physicians, researchers or other medical professionals who influence their peers' medical practice, including but not limited to prescribing behavior. Pharmaceutical companies may hire KOLs to consult for them, conduct clinical trials, give lectures and seminars, and occasionally to make presentations on their behalf at FDA regulatory hearings. KOLs are generally determined from reviewing literature or surveying professionals in the field. However, such techniques are time consuming and often generate results that are difficult to explore and/or quantify.

SUMMARY OF THE INVENTION

A method of generating, storing and mining data related to key opinion leaders in scientific fields is provided. The method includes extracting published works data, individual data, organization data and subject matter data for a plurality of published scientific works to identify entities for each of the published scientific works and storing the published works data, the individual data, the organization data and the subject matter data in a graph database as an explorable network in which each of the entities is represented by a respective node, the published scientific works including at least one of results of clinical trials and biomedical scientific publications, the entities including the published scientific works, individuals, organizations and subjects, the nodes including published work nodes representing the published scientific works, individual nodes representing the individuals, organization nodes representing the organizations and subject matter nodes representing the subjects, each of the individual nodes being linked to at least one of the other individual nodes, at least one of the organization nodes and at least one of the subject matter nodes, the graph database being configured such that the individual nodes, organization nodes and subject nodes are each displayable on a graphical user interface as a center node icon in a partial view of the explorable network with linked nodes being generated as outer node icons surrounding the center node icon; mining the explorable network stored in the graph database to augment the explorable network with supplemental information for each individual in the explorable network, the supplemental information being relevant to each individual being a key opinion leader and including at least one of: a number of the biomedical scientific publications authored by each individual in the explorable network, a number of direct links for each individual in the explorable network with other individual entities in the explorable network based on the biomedical scientific publications, a number of citations acquired through the biomedical scientific publications for each individual in the explorable network, a number of the biomedical scientific publications in which each individual in the explorable network was positioned as the last author, a number of the clinical trials in which each individual in the explorable network participated as an investigator, a number of reviews in the biomedical scientific publications authored by each person in the explorable network, a number of guidelines or practice guidelines in the biomedical scientific publications authored by each person in the explorable network, and an earliest data for a publication in the biomedical scientific publications for each person in the explorable network; and storing the supplemental information for each individual in the explorable network such that upon selection of a node icon representing one or more of the individual node icons the corresponding supplemental information for the one or more individuals represented by the one or more individual nodes is generated on the graphical user interface.

In one or more preferred embodiments, organization nodes, published work nodes and subject matter nodes can also include supplemental information. For organization nodes, the supplemental information can include the number of individuals associated with a respective organization, more specifically, the number of authors of biomedical scientific publications affiliated with the respective organization together with the number of investigators of clinical trials affiliated with the respective organization where publications affiliated with the respective organization are the number of publications authored by researchers affiliated to the respective organization and clinical trials affiliated with the respective organization are the number of trials organized and/or sponsored by the respective organization. For published works nodes representing biomedical scientific publications (i.e., publication nodes), the supplemental information can include, for a respective scientific publications, the number of times the respective publication was cited in other publications (i.e., a citation metric). For published works nodes representing clinical trials (i.e., clinical trial nodes), the supplemental information can include, for a respective trial, the number of sites in which the respective trial recruited patients (i.e., a site metric). For subject matter nodes, the supplemental information can include the number of publications on the respective subject in the graph database (i.e., a knowledge metric) and/or the number of trials organized on the respective subject in the database (i.e., a feasibility metric) and/or the number of researchers (authors and investigators) active on the subject (i.e., a community metric).

A method of generating an explorable network stored in a graph database in a graphical user interface is also provided. The method includes displaying, by a computer system, the graphical user interface on a client computer; accessing, in response to a user input from the client computer in an input section of the graphical user interface, nodes representing entities stored in the graph database and generating a first partial view of the explorable network in a graph explorer section of the graphical user interface, the entities including individuals, organizations and subjects related to published scientific data for a plurality of published works, the user input specifying at least one of the entities, the first partial view including a first center node icon representing the at least one user input entity and a plurality of first outer node icons each representing other entities linked to the at least one input entity in the graph database; displaying, in response to a user selection of one of the center node icon or the outer node icons, each of the entities represented by the selected node icon and corresponding supplemental information in a respective subsection of a supplemental information section of the graphical user interface, the supplemental information for the individuals being relevant to each individual being a key opinion leader; and generating, in response to a user selection of one of the subsections of the supplemental information section, a second partial view of the explorable network is generated in the graph explorer section, the second partial view including a second center node icon representing the entity displayed in the selected subsection and a plurality of second outer node icons each representing other entities linked to the entity displayed in the selected subsection in the graph database.

A computer system configured for generating an explorable network stored in a graph database in a graphical user interface is also provided. The computer system includes a data structure storing a graph database including data extracted from published scientific data for a plurality of published scientific works and including individual data, organization data and subject matter data identifying entities for each of the published works. The published works includes at least one of results of clinical trials and biomedical scientific publications. The entities include the published scientific works, individuals, organizations and subjects. The individual data, organization data and subject matter data are stored in the graph database as an explorable network including a plurality of nodes in which the individuals are represented by individual nodes, the organizations are represented by organization nodes and the subjects are represented by subject matter nodes. Each of the individual nodes is linked to at least one of the other individual nodes, at least one of the organization nodes and at least one of the subject matter nodes. The computer system also includes a processor configured to control the computer system to: display the graphical user interface on a client computer; access, in response to a user input from the client computer in an input section of the graphical user interface, the nodes representing entities stored in the graph database and generating a first partial view of the explorable network in a graph explorer section of the graphical user interface, the user input specifying at least one of the entities, the first partial view including a first center node icon representing the at least one user input entity and a plurality of first outer node icons each representing other entities inked to the at least one input entity in the graph database; display, in response to a user selection of one of the center node icon or the outer node icons, each of the entities represented by the selected node icon and corresponding supplemental information in a respective subsection of a supplemental information section of the graphical user interface, the supplemental information for the individuals being relevant to each individual being a key opinion leader; and generate, in response to a user selection of one of the subsections of the supplemental information section, a second partial view of the explorable network is generated in the graph explorer section, the second partial view including a second center node icon representing the entity displayed in the selected subsection and a plurality of second outer node icons each representing other entities linked to the entity displayed in the selected subsection in the graph database.

In further embodiments, computer readable media are provided which have stored thereon, computer executable process steps operable to control a computer to perform the methods described above.

BRIEF DESCRIPTION OF THE DRAWINGS

The present invention is described below by reference to the following drawings, in which.

DETAILED DESCRIPTION

The present disclosure provides a complete influencer analytics solution that can help with KOL identification, mapping and profiling as well as talent recruitment. By extracting and organizing data from a database of abstracts on biomedical scientific literature, for example PubMed, and a registry of clinical trials, for example ClinicalTrials.gov—hosted by the United States government, from the perspective of researchers and organizations, systems and methods in accordance with embodiments of the present application can enable multidisciplinary teams to unravel networks illustrating connections between entities, including people and organizations. The present disclosure involves generating specific information from scientific data sources, creating informative metrics and linking the information and metrics together to define an explorable network that allows a user to quickly and effectively browse through the explorable network to pinpoint individuals and organizations having expertise in scientific fields. The explorable network quantifies individuals and organizations and links them to scientific subjects for the practical application of identifying key opinion leaders for talent recruitment.

The present disclosure also provides an analytical tool usable to analyze any scientific domain that can be characterized through scientific publications and/or clinical trials.

Although the particular software, programming languages and techniques, and architecture described exemplary embodiments described below are particularly advantageous, a person of ordinary skill in the art will appreciate that other software, programming languages and techniques and architectures may alternatively be used. For example, although XML files are described below, other file formats may be used.

Figure 1A:
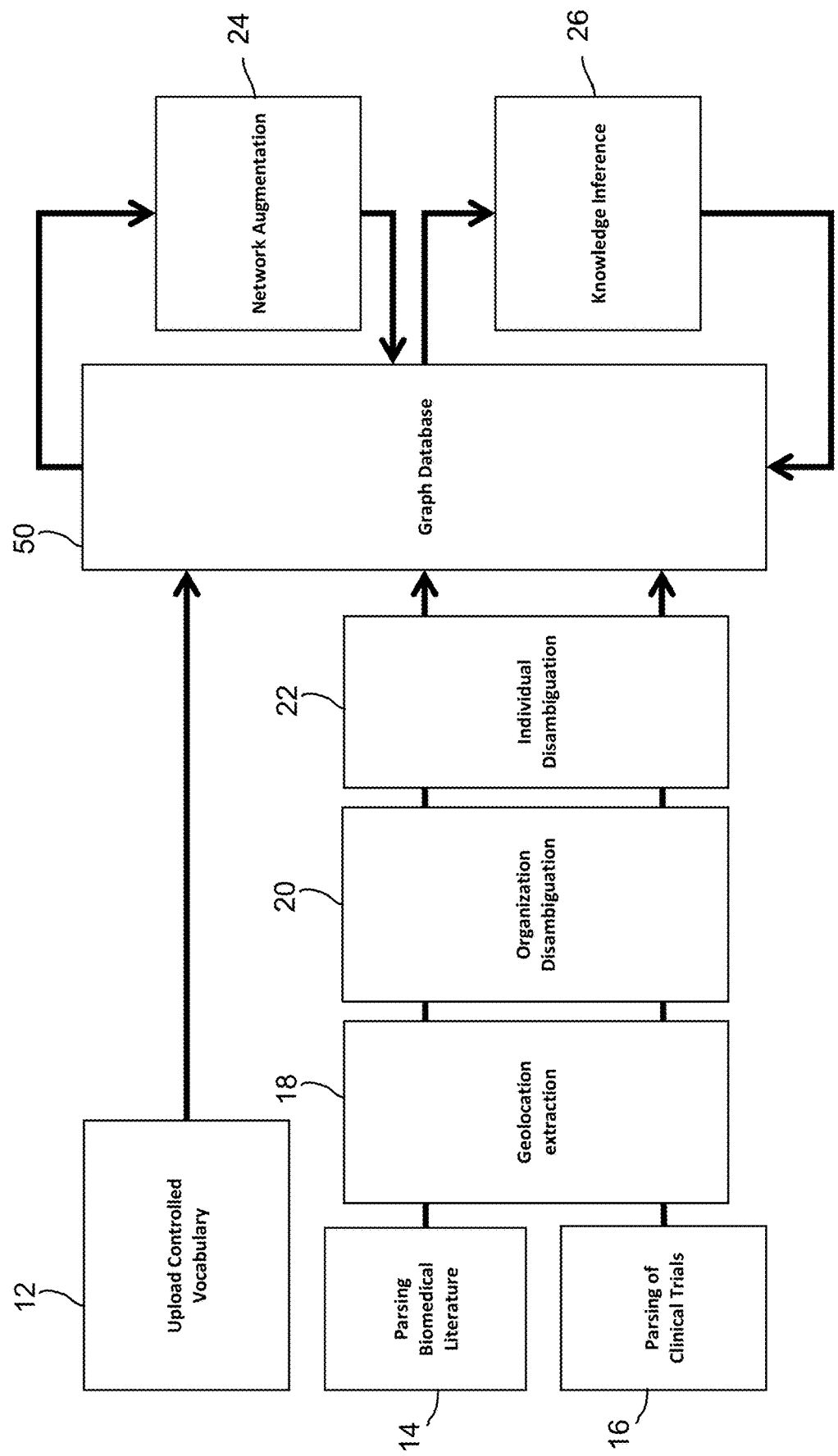
FIG. 1a schematically shows a flow chart of a method of storing and ingesting data to generate a graph database in accordance with an embodiment of the present invention.

FIG. 1a schematically shows a flow chart of a method 10 of generating, storing and mining data to generate an explorable network in a graph database in accordance with an embodiment of the present invention. Method 10 first includes steps 12 to 22 that involve extracting published works data, individual data, organization data and subject matter data for a plurality of published works to identify entities for each of the published works and storing the published works data, the individual data, the organization data and the subject matter data in a graph database as an explorable network in which each of the entities is represented by a respective node. In the example embodiment described with respect to steps 12 to 22, the published works include results of clinical trials and biomedical scientific publications and the published scientific data include the scientific abstracts available on PubMed and the clinical trials data available from ClinicalTrials.Gov.

Method 10 includes a step 12 of uploading a controlled vocabulary into a graph database 50. The controlled vocabulary includes descriptors, also known as subject headings, that are arranged in both an alphabetic structure and hierarchal structure, i.e., an ontology. The controlled vocabulary may also include a short description or definition of each descriptor, which includes synonyms. In a preferred embodiment, the controlled vocabulary is medical subject headings ("MeSH"), which is a comprehensive controlled vocabulary for the purpose of indexing journal articles and books in the life sciences to serve as a thesaurus that facilitates searching. MeSH was created and updated by the United States National Library of Medicine (NLM) and is used by the MEDLINE/PubMed publication database and by NLM's catalog of book holdings. MeSH is also used by ClinicalTrials.gov registry to classify which diseases are studied by trials registered in ClinicalTrials.gov.

Figure 2:
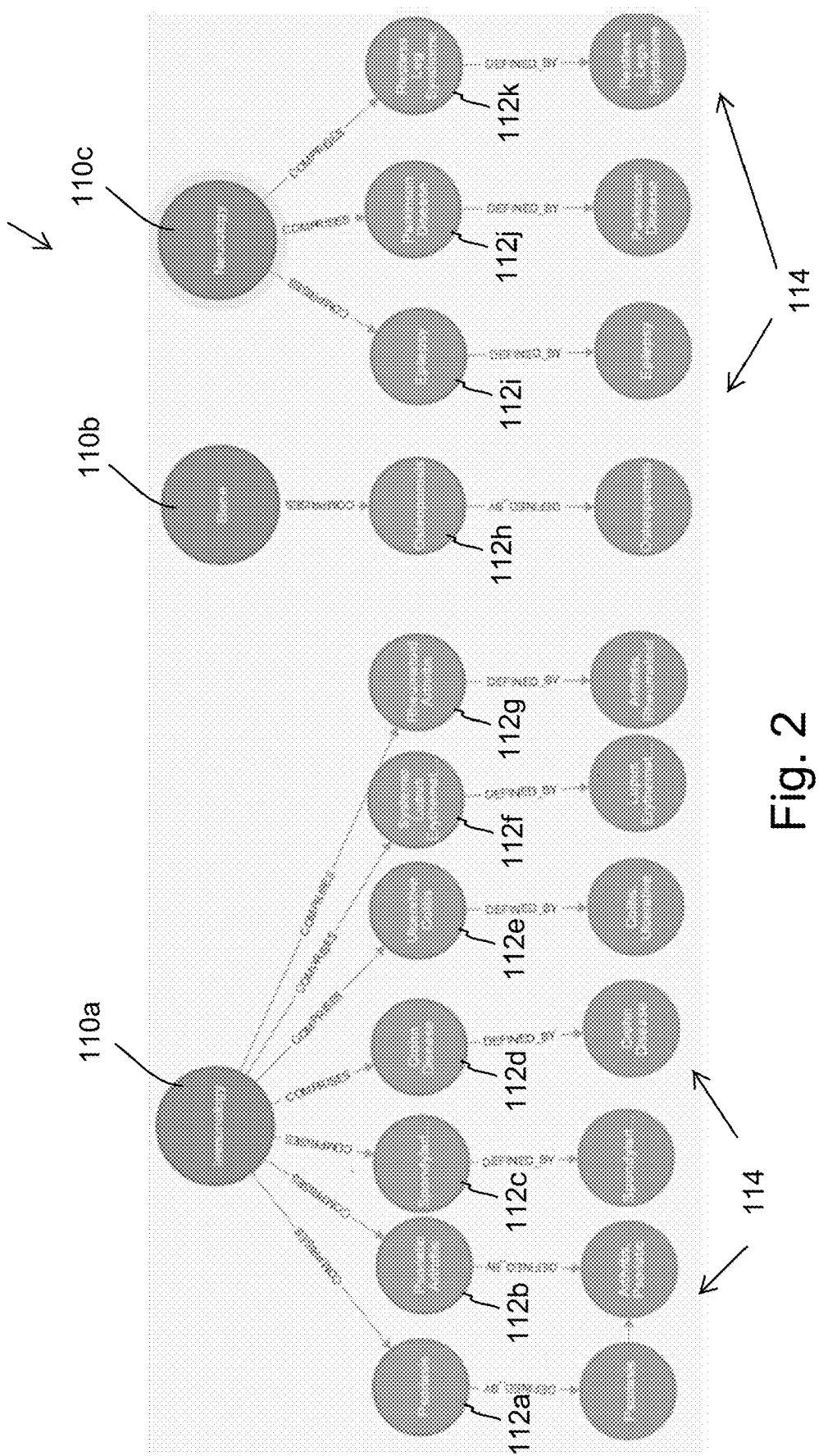
FIG. 2 schematically shows a graphical depiction of hierarchical structure of an exemplary ontology in accordance with an embodiment of the present invention.

The MeSH controlled vocabulary is used to define subdomains of interest, which herein are defined as any kind of research focus in the field of biomedical science, in the resulting graph database 50. Accordingly, the present disclose involves, in addition to identifying KOLs in a certain therapeutic area or disease, identifying experts in a specific scientific niche (e.g., Interleukin-17 related diseases). The entire version 2016 of the MeSH controlled vocabulary is currently downloadable as XML files from www.nlm.nih.gov/mesh. The MeSH controlled vocabulary uploaded into graph database 50 includes thousands of descriptors and the corresponding ontology includes hierarchical connections between the descriptors. In addition to the description and their hierarchical connections, to provide more specific entry points, additional categories of therapeutic areas and diseases are added to the hierarchical structure of the ontology, an example of which is graphically illustrated in FIG. 2, and stored in graph database. In other words, the hierarchal structure is supplemented with diseases and therapeutic areas, with the diseases being a subcategory of the therapeutic areas and the descriptors being a subcategory of the diseases. The hierarchical structure of therapeutic areas and diseases can be created based on a medical expert's understanding of the concepts. In one preferred embodiment, the therapeutic areas and diseases are added to the ontology of the controlled vocabulary immediately after the MeSH controlled vocabulary is uploaded into graph database 50. (Box 12 of FIG. 1*a*). For example, a first therapeutic area 110*a* of immunology includes a plurality of diseases 112*a* to 112*g* including psoriasis, psoriatic arthritis, Crohn's disease, spondyloarthritis, ulcerative colitis, lupus erythematosus and rheumatoid arthritis categorized within immunology, a second therapeutic area 110*b* of bone includes a disease 112*h* of osteoporosis and a third therapeutic area 110*c* includes diseases 112*i* to 112*k* of epilepsy, Parkinson's disease and restless leg syndrome. Each disease 112 to 112*k* is defined by at least one descriptor 114.

The descriptors define topics, which along with the diseases and therapeutic areas, are entities of the subject matter data. The storing of the controlled vocabulary creates subject matter nodes within graph database 50, with a subject matter node being created for each subject matter entity within the controlled vocabulary in accordance with the hierarchal structure of the controlled vocabulary. The subject matter nodes include a plurality of topic nodes, a plurality of disease nodes and a plurality of therapeutic area nodes. For each topic node created, a disease node is created for each disease linked to the descriptor in the hierarchal structure of the controlled vocabulary and a therapeutic area node is created for each therapeutic area linked to the descriptor via the disease in the hierarchal structure of the controlled vocabulary.

Step 14 includes parsing biomedical scientific literature to extract published works data, individual data, organization data and subject matter data. As noted above, in one preferred embodiment, the biomedical scientific literature is in the form of scientific abstracts from PubMed. Scientific abstracts of interest are currently downloadable as XML files from http://www.ncbi.nlm.nih.gov/pubmed. The scientific abstracts of interest are generated by specifying a query and optionally one or more filters on PubMed. The scientific abstracts may be downloaded as individual XML files and sorted on PubMed identifiers ("PMIDs") using XQuery so that the abstracts in an XML file are approximately ranked in ascending order according to the date of publication.

Examples of queries for diseases with date filters are shown below in Table 1.

TABLE 1

| Source | Query | Filter | Number of publications |
|---|---|---|---|
| PubMed | Epilepsy [MH] | From 01 JAN 2000 onwards | 63,110 |
| PubMed | Parkinson Disease [MH] | From 01 JAN 2000 onwards | 31,476 |
| PubMed | Restless Leg Syndrome [MH] | From 01 JAN 2000 onwards | 2,271 |
| PubMed | Inflammatory Bowel Diseases [MH] | From 01 JAN 2000 onwards | 34,366 |
| PubMed | Lupus Erythematosus, Systemic [MH] | From 01 JAN 2000 onwards | 21,373 |
| PubMed | (Bone Diseases, Metabolic [MH] OR Osteoporotic Fractures [MH]) AND Eng [LA] | From 01 JAN 2000 onwards | 31,880 |
| PubMed | Arthritis, Rheumatoid [MH] | From 01 JAN 2000 onwards | 39,621 |
| PubMed | Spondylarthritis [MH] | From 01 JAN 2000 onwards | 9,945 |
| PubMed | Arthritis, Psoriatic [MH] | From 01 JAN 2000 onwards | 3,209 |
| PubMed | Psoriasis [MH] | From 01 JAN 2000 onwards | 14,480 |

The XML files associated with a disease are processed one by one and all relevant metadata on a publication is extracted from the XML: publication identifier (PMID), journal name, date of publication, title, MeSH descriptors with which the publication is tagged, name of authors (first and last name separated) and an affiliation string include the affiliations of the authors. The publication identifier (PMID), journal name, date of publication, title define published works data for each publication, the MeSH descriptors define subject matter data for each publication, the name of authors define individual data for each publication and the affiliation strings define organization data for each publication and location data for each organization and/or individual in accordance with step 18.

The affiliation string includes e-mail addresses, names of organizations and professional whereabouts of the authors as free text. For the extraction of information from the affiliation string, a custom built parser, developed for example in Python programming language, uses regular expression patterns to disentangle the separate components embedded in the free text. For each class of derivable information in the affiliation string a set of patterns is used to locate them in the string and extract this information, e.g. e-mail addresses are defined by the following regular expression pattern: .\.? [\s\p{L}]*:?\s*([a-z0-9!#$%&'*+V =?^_'{|}~-]+(?:\.[a-z0-9!#$%&'*+V =?^_'{|}~-]+)*@(?:[a-z0-9](?:[a-z0-9-]*[a-z0-9])?(\.l\sdot\s))+[a-z0-9](?:[a-z0-9-]*[a-z0-9])?). These XML files are processed using an event-based Simple API for XML ("SAX") interface to XML to be able to handle massive XML files.

A published work node is created for each publication and each published work is linked to a topic node for each unique descriptor in the respective publication, with each published work node being directly linked to the topic nodes representing descriptors with which the publication is tagged. Accordingly, each publication node is linked to the corresponding disease nodes and therapeutic area nodes via the topic nodes directly linked to the publication node.

The individual data, organization data and location data from the biomedical scientific literature is processed in steps 18 to 22 to create individual nodes, organization nodes and location nodes.

Method 10 further includes a step 16 of parsing clinical trial records to extract information. As noted above, in one preferred embodiment, the clinical trial records are in the form of clinical trial entries of interest downloaded from ClinicalTrials.gov, which is a registry and results database of publicly and privately supported clinical studies of human participants conducted around the world and hosted by the US government. All study and results fields for the clinical trials of interest are currently downloadable as a zipped archives containing an XML file for each trial in query result using the web frontal: https://clinicaltrials.gov. The scientific abstracts of interest are generated by specifying a query and optionally one or more filters on ClinicalTrials.gov. Examples of queries for diseases with date filters are shown below in Table 2.

TABLE 2

| Source | Query | Number of trials |
|---|---|---|
| ClinicalTrials.gov | Epilepsy | 1,008 |
| ClinicalTrials.gov | Parkinson Disease | 1,447 |
| ClinicalTrials.gov | Restless Leg Syndrome | 150 |
| ClinicalTrials.gov | Inflammatory Bowel Diseases | 1,283 |
| ClinicalTrials.gov | Systemic Lupus Erythematosus | 467 |
| ClinicalTrials.gov | Metabolic Bone Diseases | 786 |
| ClinicalTrials.gov | Arthritis | 4,420 |
| ClinicalTrials.gov | Psoriasis | 974 |

In a similar manner as step 14, the following information is extracted from individual clinical trial entries: identifier (NCT), title, phase, study design, conditions, interventions, status, enrollment, start and completion date, MeSH descriptors for conditions and interventions and references to publications disclosing the results. In one preferred embodiment, this information is extracted using a custom written script, for example a script in the Python language, that relies on the same techniques as used for parsing PubMed XML files, i.e. regular expression parsing.

The name and the location of the organizations including universities, hospitals and pharmaceutical companies that sponsor and/or organize these trials and the principal investigators that recruited patients are also extracted. This information is not directly extractable from the primary source as the name of the organization sponsoring the trail or the organization acting as the trial site (trial sites are a type of organization, i.e., organization can be labelled "TrialSite"), and the investigators are not uniformly mapped to the available XML schema elements. To distinguish investigators from company and hospital names in ClinicalTrials.gov, the Stanford's Named Entity Recognizer (http://nlp.stanford.edu/software/CRF-NER.shtml) is used together with a dictionary of suffixes and prefixes that are the tell-tail mark for some of these categories to increase the accuracy of the NER. In addition, the name of the investigator is given as free text. Therefore, first and last name breakdown is achieved via the python package nameparser (version 0.4.0).

The identifier (NCT), title, phase, study design, conditions, interventions, status, enrollment, start and completion date and references to publications disclosing the results define published works data for each clinical trial, the MeSH descriptors define subject matter data for each clinical trial, the names of the investigators define individual data, the names of the organizations define the organization data in accordance with step 18.

A published work node is created for each publication and a topic node is created for each unique descriptor in the publications, with each published work node being directly linked to the topic nodes representing descriptors with which the publication is tagged. For each topic node created, a disease node is created for each disease linked to the descriptor in the hierarchal structure of the controlled vocabulary and a therapeutic area node is created for each therapeutic area linked to the descriptor via the disease in the hierarchal structure of the controlled vocabulary. Accordingly, each publication node is linked to the corresponding disease nodes and therapeutic area nodes via the topic nodes directly linked to the publication node.

The individual data, organization data and location data from the clinical trial records is processed in steps 18 to 22 to create individual nodes, organization nodes and location nodes.

After steps 14, 16, method 10 further includes a step 18 of extracting professional whereabouts and the mapping to geolocation, which in a preferred embodiment is in the form of the latitude and longitude coordinates, from the free text affiliation field.

Figure 1B:
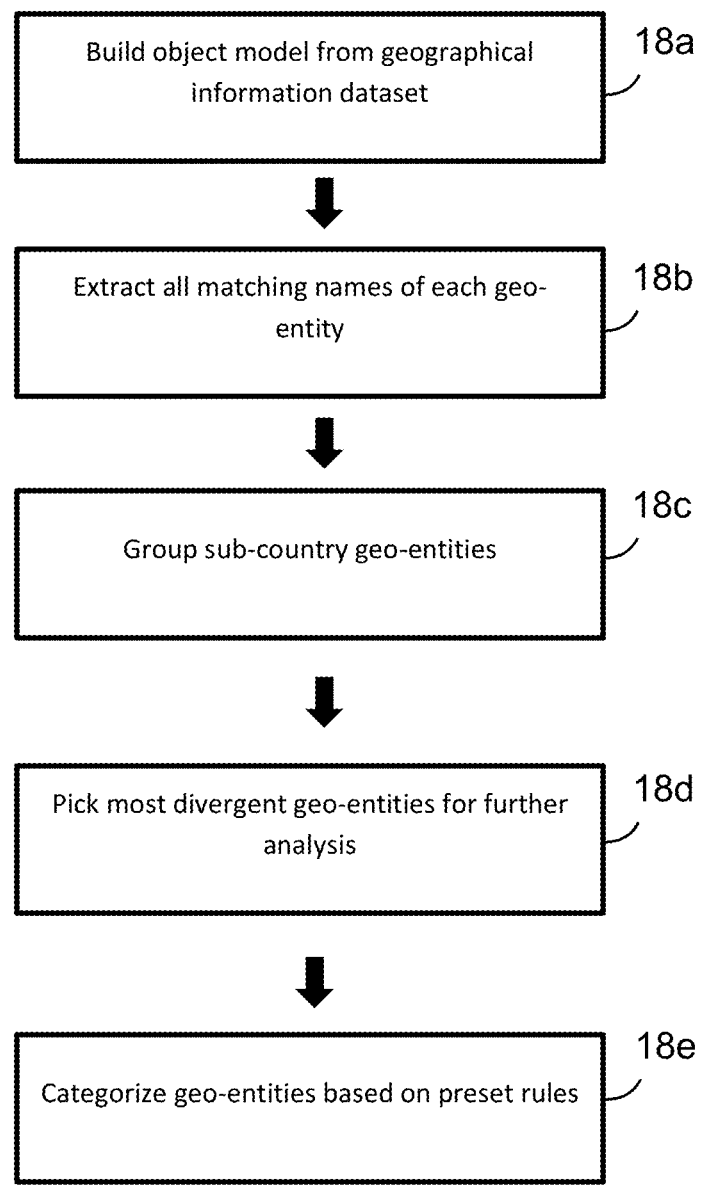
FIG. 1b shows substeps of a technique for extracting professional whereabouts and mapping to geolocation in accordance with an embodiment of the present invention.

As shown in FIG. 1b, the algorithm of step 18 includes a first substep 18a of building an in-memory object model from geographical information dataset accessible from a geographical information database. The results of step 18 are used to create location nodes that are directly linked to organization nodes. The in-memory object model can be a rich in-memory object model, with "rich" meaning that it uses concepts from the Object Oriented Programming Paradigm, i.e. the in-memory object model is based on a class diagram that utilizes modelling concepts such as inheritance. In a preferred embodiment, the geographical information dataset is in the form of a geographical dictionary downloadable from geonames.org Gazetteer at http://download-.geonames.org/export/dump/cities1000.zip.

This dataset provides metadata on geopolitical entities necessary to extract geolocations from free text. The information available on these entities is: latitude, longitude, population, administrative level (country, state, capital, city), international codes and synonyms.

The object model conforms to a predefined class diagram. Every city, state or country is represented by an object and links between cities and their state or country and states to their countries are built in as references.

In a second substep 18*b*, all matching names to geopolitical entities, aka geo-entities, i.e. cities, states and countries, are extracted from the affiliation string using case insensitive word matching. The object model is configured to contain all known synonyms and aliases for these geoentities (e.g., Gent, Gand and Ghent all map to the same geo-entity), which empowers the algorithm to detect geoentities in different languages.

In a third substep 18*c*, all sub-country geo-entities, including cities and states, are grouped based on the country in which the respective sub-country geo-entities are located.

In a fourth substep 18*d*, if more than one group of entities is present, the most divergent and consistent collection of geopolitical entities is picked for further analysis. Divergence is defined as the number of different types of geopolitical entities (cities, states, cities) present in the collection.

In a fifth substep 18*e*, an entry is picked from the selected collection according to the following rules:

a) Cities are favored over states. States are favored over countries.

b) If more than one geopolitical entity remains the one with highest administrative level is favored.

c) If more than one geopolitical entity remains and they all have the same administrative level, than the one with the highest population is favored.

After steps 14, 16, method 10 further includes an organization disambiguation step 20 to clarify the identity of the organization associated with an individual authoring the publication or listed as an investigator in a clinical trial entry as indicated in the organization metadata. For example, the extracted name of an organization from PubMed or ClinicalTrials.gov (i.e. after removal of addresses or e-mails) can be classified as at least one of hospital, university or company based on a predefined list of patterns:

TABLE 3

| Class of organization | Pattern examples |
| --- | --- |
| Hospital | Hospital, hospitals, clinic, hopital, krankenhauser, "\bCHU\b". . . |
| University | research, university, school, college, academy, universite, . . . |
| Company | company, companies, compania, enterprise, societe, "\bco\.", limited, "\bltd\b", "\bltd\.", . . . |

Step 20 includes creating a taxonomy for pharmaceutical companies, which maps several synonymous names of these companies to a single normalized name. Regular expressions are used in this taxonomy to capture the various phrasings of the company name, such that a single organization node is created for each organization. In addition, subsidiaries and historical acquisitions are mapped to their owning company to limit a number of organization nodes created.

For example, the taxonomy may include the top pharmaceutical companies based on their revenue in one or more recent years and an organization can be assigned more than one class. For example, an organization can be assigned to the class of company and may also be assigned to a class within company, such as a "big pharmaceutical company" (labelled for example as "BigPharma" for having a revenue above a specified threshold over a specified time period) based on the patterns defined in the company taxonomy for the life sciences.

After steps 14, 16, method 10 further includes an individual disambiguation step 22 to clarify the identity of the individuals associated with the publication or clinical trial entry as indicated in the individual metadata, so that multiple individual nodes are not created for the same individual. Individual disambiguation within a data source and across data sources may be helpful because of homonymy existing in the space of researchers' names (i.e. two researchers active in a different scientific domain, or even worse in the same domain, can have the same name) and because of inconsistencies and misspellings in names provided in these sources (i.e. the same researcher can have slightly different author names in use in its publications). Each of the names generated by parsing the published scientific data is compared with names of individuals represented by existing individual nodes within the graph database to determine whether each individual related each of the published scientific works is represented by one of the existing individual nodes. If an individual is not represented by an existing individual node, a new individual node is created for the individual, which is then directly linked to the published works node for the respective published scientific work. If an individual is represented by an existing individual node, the existed individual node is directly linked to the published works node for the respective published scientific work.

The algorithm that disambiguates authors and investigators uses informational cues in the name itself as well as information that can be derived from the collaborative network.

Figure 1C:
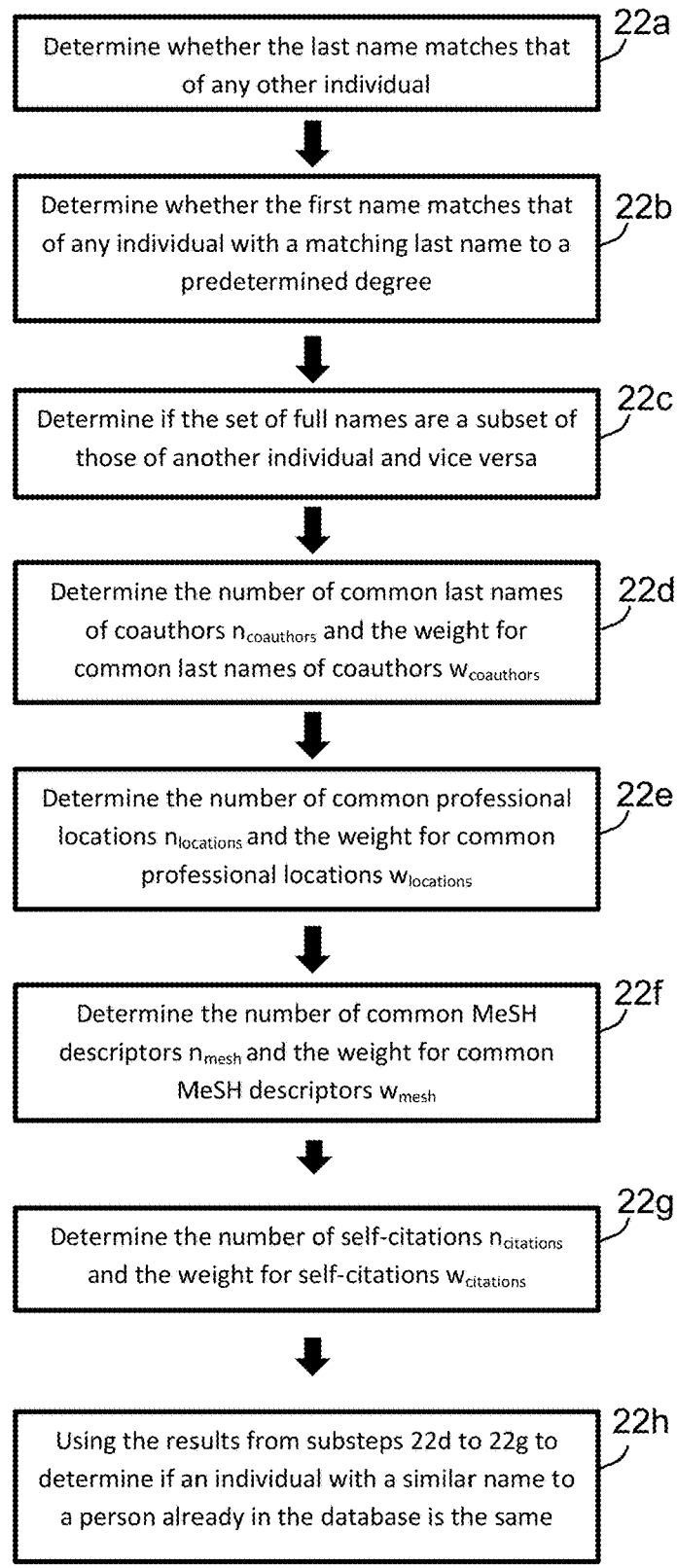
FIG. 1c shows substeps of a name comparison technique in accordance with an embodiment of the present invention.

Step 22 first includes a name comparison, which involves comparing a name to be clarified with existing names stored in graph database 50 as individual nodes. More specifically, a name of an author of a new publication or the name of an investigator of a new clinical trial can only match an existing person in the database if and only if the names are similar enough. The name comparison algorithm analyzes the first and last name as separate entities. In a preferred embodiment, the last name is matched exactly, but the first name can be matched in a lenient or more stringent way. The substeps of step 22 are shown in FIG. 1*c*. In other words, the name comparison algorithm includes a first substep 22*a* of step 22 of determining whether the last name of the individual at issue exactly matches the last name of any of the other individual represented in the individual data. The name comparison then includes a second substep 22*b* of determining whether the first name of the individual at issue matches the first name of the individuals with the matching last name to a predetermined degree. The predetermined degree can be either a lenient degree or a stringent degree. For the lenient degree of first name matching, the initials derived from first names and middle initials, if applicable, for the individual at issue are considered as matching with an individual if the initials derived from first names and middle initials overlap (e.g., Jan E, Taes (first instance of the last name)=Jan, Taes (second instance of the last name)). The initials derived from first names and middle initials overlap if the ordered list of initials of one name are identical to the other name's list of initials. The size of the longest list is truncated (i.e. elements are removed from the tail) such that the size of both lists are identical. For this example, the first instance of the name—Jan E. Taes—is shortened to Jan Taes because the second instance does not include a middle initial. This boils down to the looking for an overlap between these lists starting from the head of these lists.

For the stringent degree of first name matching, the initials derived from first names and middle initials, if applicable, for the individual at issue are considered as matching with an individual if the initials derived from first names and middle are identical (e.g., Jan E, Taes< >JJan, Taes). Initials derived from first names and middle initials need to be identical for the two names that are compared. Lastly, the name comparison includes a third substep 22c of determining if the set of full first names of the individual are a subset of the those of another individual and vice versa (e.g., Jean Lester, Kauff< >Jean Len, Kauff and Jonathan J, Kauff=Jonathan John, Kauff). If all three sub steps 22a to 22c are satisfied, the individuals are considered as passing the name comparison phase.

After the name comparison, step 22 then includes a network comparison phase, which involves using additional network to identify an individual at issue as being identical to an individual already in the database. The network comparison phase and name comparison phase need both to result in a positive match before individuals are considered to be the same physical person in reality.

In a preferred embodiment, the network comparison includes a substep 22d of determining the number of common last names of coauthors $n_{coauthors}$ and the weight for common last names of coauthors $w_{coauthors}$. Each weight in the network comparison phase is a floating point number that can be arbitrarily set when configuring the ingestion pipeline. In this particular implementation this weight is set based on a benchmark. For example, if Jean Marc, Kauff co-authored with Jan, Taes and R, Goemaere in a publication of 2010, the last names of these co-authors are used by the algorithm to decide that Jean, Kauff as author of a publication in 2015 is the same person as Jean Marc, Kauff from the 2010 publication based on the fact that again, for the 2015 publication, Taes and Goemaere appear as co-authors.

The network comparison also includes a substep 22e of determining the number of common professional locations $n_{locations}$ and the weight for common professional locations $w_{locations}$. For example, Jean Marc. Kauff who authored a publication through his affiliation to the University of Ghent is considered to be identical to J, Kauff who published another publication again through an affiliation with an organization located in Ghent.

The network comparison also includes a substep 22f of determining the number of common MeSH descriptors $n_{mesh}$ and the weight for common MeSH descriptors $w_{mesh}$. For example, Jean Marc, Kauff who authored a publication in 2010 tagged with the MeSH Descriptor "Osteoporosis" is considered to be the same author as J M, Kauff who published a publication in 2015 which is again tagged with the descriptor "Osteoporosis".

The network comparison also includes a substep 22g of determining the number of self-citations $n_{citations}$ and the weight for self-citations $w_{citations}$. For example, J M, Kauff as author of publication A is identical to J, Kauff who authored a publication B because publication A makes a citation to a publication already in the database that is authored by J, Kauff.

Finally, after substeps 22d to 22h, a substep 22h includes using the following formula to determine if an individual with a similar name to a person already in the database is the same person:

$$n_{coauthors}*w_{coauthors}+n_{locations}*w_{locations}+n_{mesh}*w_{mesh}+n_{citations}*w_{citations} \geq threshold_{match}$$

If the resulting score of all the additional network cues is greater than the predefined $threshold_{match}$, then the new individual is considered identical to the individual already in the database.

The network comparison algorithm of substeps 22d to 22i is fully customizable by the aforementioned options and weights. Because homonymy is an even more severe problem for Asian researchers, the algorithm may use a different set of parameters for Asian names than for Western names. To decide to which namespace a researcher belongs the last name of the author can assessed for presence in a predefined list of Asian last names. Additionally, a corrections table may be maintained that provides additional information to the algorithm so that known remaining mismatches can be corrected.

Steps 14 to 22 result in individual data, organization data and subject matter data being stored in graph database 50 as an explorable network. Each entity in the individual data, organization data and subject matter data is stored as a node and the nodes are linked by edges in accordance with the determinations made in steps 14 to 22. In one preferred embodiment, the individuals include authors of the biomedical scientific publications and investigators in the clinical trials as mentioned in steps 14 and 16. Also, the organizations include hospitals, universities and companies as mentioned above in step 20. The subjects include publication information including the biomedical scientific publications, the investigated topics of the biomedical scientific publications, the diseases of the biomedical scientific publications and the therapeutic areas of the biomedical scientific publications. The subjects also include clinical trial information including the clinical trials, investigated topics of the clinical trials, diseases of the clinical trials and therapeutic areas of the clinical trials. The links between the entities are determined based on the publication information, the clinical trial information and the controlled vocabulary and corresponding ontology.

Each entity in the individual data (i.e., each individual), is connected to at least one entity in the organization data (i.e., at least one organization) and at least one entity in the subject matter data (i.e., at least one subject) based on the publications and clinical trials. In one preferred embodiment, as a general rule, an organization is directly linked only to an individual. The only exception to this rule is with respect to clinical trials, which can be directly linked to an organization acting as the trial site for the clinical trial. Every link between an organization and an individual is stored in the database, including the historical links and the current links (i.e., the time of an individual's link to an organization is stored as a property of the link based on for example the individual's employment history). Each publication node and each clinical trial node is directly connected to at least one individual node and at least one subject matter node in graph database 50. Topic nodes, a subgroup of subject matter nodes representing MESH descriptors, are directly linked to the publication nodes and/or the clinical trial nodes and the disease nodes and therapeutic area nodes, subgroups of subject matter nodes added to graph database in step 12, are indirectly linked to the publication nodes via the topics nodes and are in turn indirectly linked to the individual nodes via the individual nodes. Two entities are considered as being linked if the two entities are directly linked or are indirectly linked via a publication or clinical trial.

For example, FIG. 1d graphically displays a links schema in accordance with an embodiment of the present invention, which is also described below in Table 3. The schema shows links between the entities, with the links representing both direct and indirect links. An exemplary individual node 113a representing an individual is linked (directly) to an exemplary publication node 113b representing a publication in which the individual authored, linked (directly) to an exemplary clinical trial node 113c representing a clinical trial in which the individual participated, linked (indirectly via the publication or the clinical trial) to an exemplary organization node 113d representing an organization in which the individual is affiliated, linked (indirectly via the publication or the clinical trial) to an exemplary topic node 113e representing a topic, e.g., as determined by a MeSH descriptor, in which the individual investigated in the clinical trial or published about in the publication, linked (indirectly via the publication or the clinical trial) to an exemplary therapeutic area node 113f representing a therapeutic area in which the individual investigated in the clinical trial or published about in the publication linked (indirectly via the publication or the clinical trial) to an exemplary disease node 113g representing a disease in which the individual investigated in the clinical trial or published about in the publication.

An exemplary individual node 113a representing an individual is linked (directly) to an exemplary publication node 113b representing a publication in which the individual authored, linked (directly) to an exemplary clinical trial node 113c representing a clinical trial in which the individual participated, linked (directly) to an exemplary organization node 113d representing an organization in which the individual is affiliated, linked (indirectly via a publication and/or a clinical trial) to an exemplary topic node 113e representing a topic, e.g., as determined by a MeSH descriptor, in which the individual investigated in a clinical trial or published about in a publication, linked (indirectly via a publication and/or a clinical trial) to an exemplary therapeutic area node 113f representing a therapeutic area in which the individual investigated in a clinical trial or published about in a publication, and linked (indirectly via a publication and/or a clinical trial) to an exemplary disease node 113g representing a disease in which the individual investigated in a clinical trial or published about in a publication.

Figure 1D:
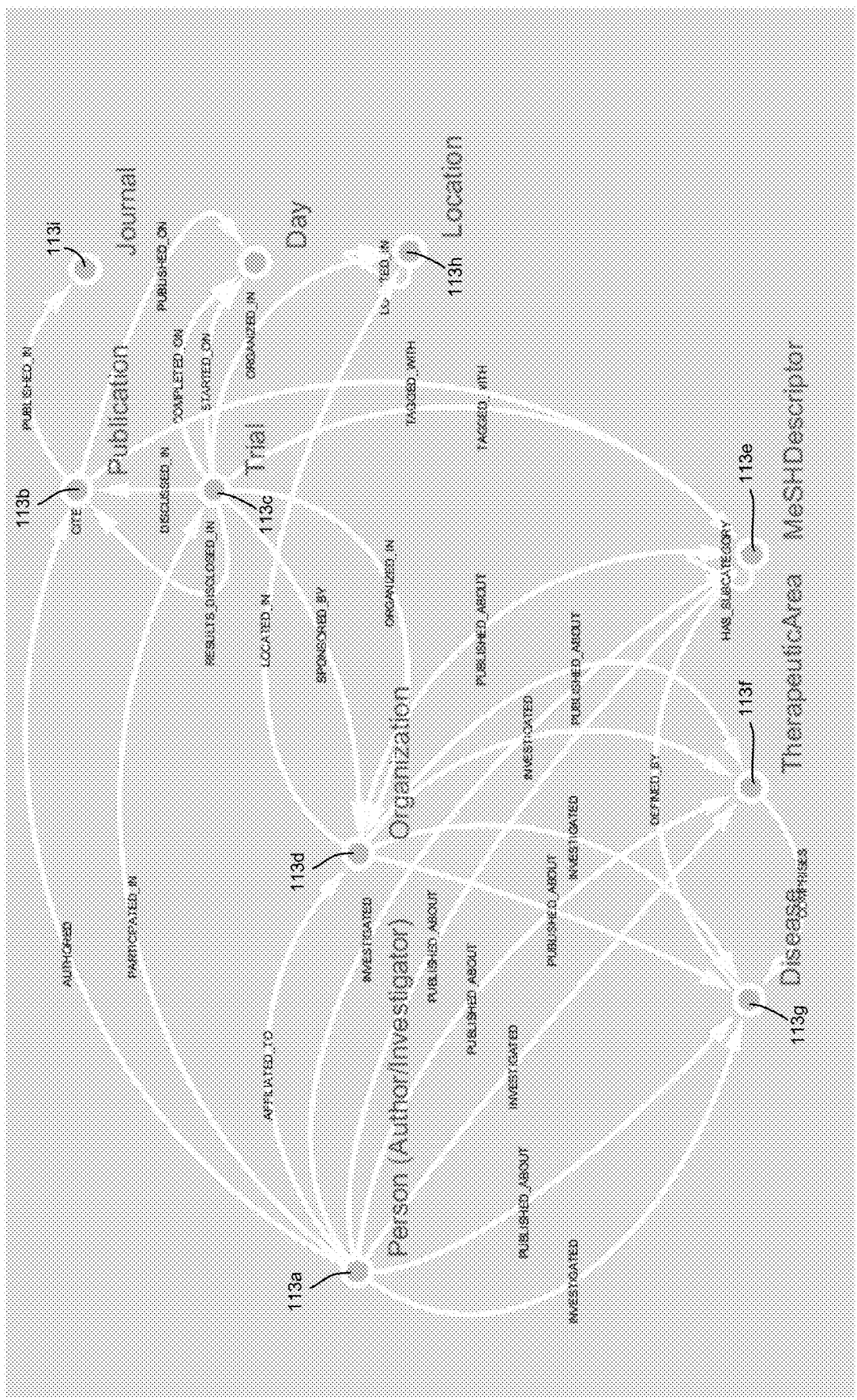
FIG. 1d graphically displays a links schema in accordance with an embodiment of the present invention.

The exemplary organization node 113d is linked (directly) to a location node 113h representing a location of the organization, linked (indirectly via an individual affiliated with the organization—in the embodiment illustrated in FIG. 1d, the link between publications and organizations is inferred from the network on the fly (via a query) without persisting this information in the graph database) to the exemplary publication node 113b, linked (indirectly via an individual sponsored by the organization or directly if the organization hosted the clinical trial) to the exemplary clinical trial node 113c, linked (indirectly via the individual and then publication or the clinical trial) to the exemplary topic node 113e, linked (indirectly via the individual and then publication or the clinical trial) to the exemplary therapeutic area node 113f, and linked (indirectly via the individual and then publication or the clinical trial) to the exemplary disease node 113g.

The exemplary disease node 113g is linked (directly) to the therapeutic area node 113f in which the disease is comprised and linked (directly) to the topic node 113e by which the disease is defined in the hierarchal structure. The exemplary therapeutic area node 113f is also (indirectly by a disease) linked to the topic node 113e based on the hierarchal structure.

Additionally, the publication node 113b is linked to the clinical trial node 113c if the trial is discussed in the publication or the results are disclosed in the publication. In the embodiment illustrated in FIG. 1d, there are two types of linkage between publications and trials: 1) the protocol of a study can be explained in a publication or the protocol can rely on techniques disclosed in cited papers; and 2) the results of a trial can be disclosed in a paper. Publication node 113b is also linked to an exemplary journal node 113i representing a journal in which the publication is published. The publication node 113b and clinical trial node 113c are also each linked to a date node 113j representing a date in which the publication was published and representing a date in which the clinical trial was completed on or started on.

TABLE 3

| SrcNode | Rel | DstNode |
|---|---|---|
| Disease | DEFINED_BY | MeSHDescriptor |
| Location | LOCATED_IN | Location |
| MeSHDescriptor | HAS_SUBCATEGORY | MeSHDescriptor |
| Person (Author/Investigator) | PUBLISHED_ABOUT | MeSHDescriptor |
| Person (Author/Investigator) | INVESTIGATED | MeSHDescriptor |
| Person (Author/Investigator) | PUBLISHED_ABOUT | TherapeuticArea |
| Person (Author/Investigator) | INVESTIGATED | TherapeuticArea |
| Person (Author/Investigator) | PUBLISHED_ABOUT | Disease |
| Person (Author/Investigator) | INVESTIGATED | Disease |
| Person (Author/Investigator) | AUTHORED | Publication |
| Person (Author/Investigator) | AFFILIATED_TO | Organization |
| Person (Author/Investigator) | PARTICIPATED_IN | Trial |
| Organization | PUBLISHED_ABOUT | MeSHDescriptor |
| Organization | LOCATED_IN | Location |
| Organization | PUBLISHED_ABOUT | TherapeuticArea |
| Organization | INVESTIGATED | TherapeuticArea |
| Organization | PUBLISHED_ABOUT | Disease |
| Organization | INVESTIGATED | Disease |
| Publication | TAGGED_WITH | MeSHDescriptor |
| Publication | CITED_BY | Publication |
| Publication | PUBLISHED_IN | Journal |
| Publication | PUBLISHED_ON | Day |
| TherapeuticArea | COMPRISES | Disease |
| Trial | TAGGED_WITH | MeSHDescriptor |
| Trial | ORGANIZED_IN | Location |
| Trial | STARTED_ON | Day |
| Trial | ORGANIZED_IN | Organization |
| Trial | SPONSORED_BY | Organization |
| Trial | DISCUSSED_IN | Publication |
| Trial | COMPLETED_ON | Day |
| Trial | RESULTS_DISCLOSED_IN | Publication |

For example, for every ingested publication the authors are created as new individual nodes or merged with existing individual nodes. These individual nodes are linked to the subject matter nodes that are linked to the ingested publication. For every MeSH descriptor with which the publication is tagged, a link is created between the publication node and the topic node representing the MeSH descriptor.

Figure 1E:
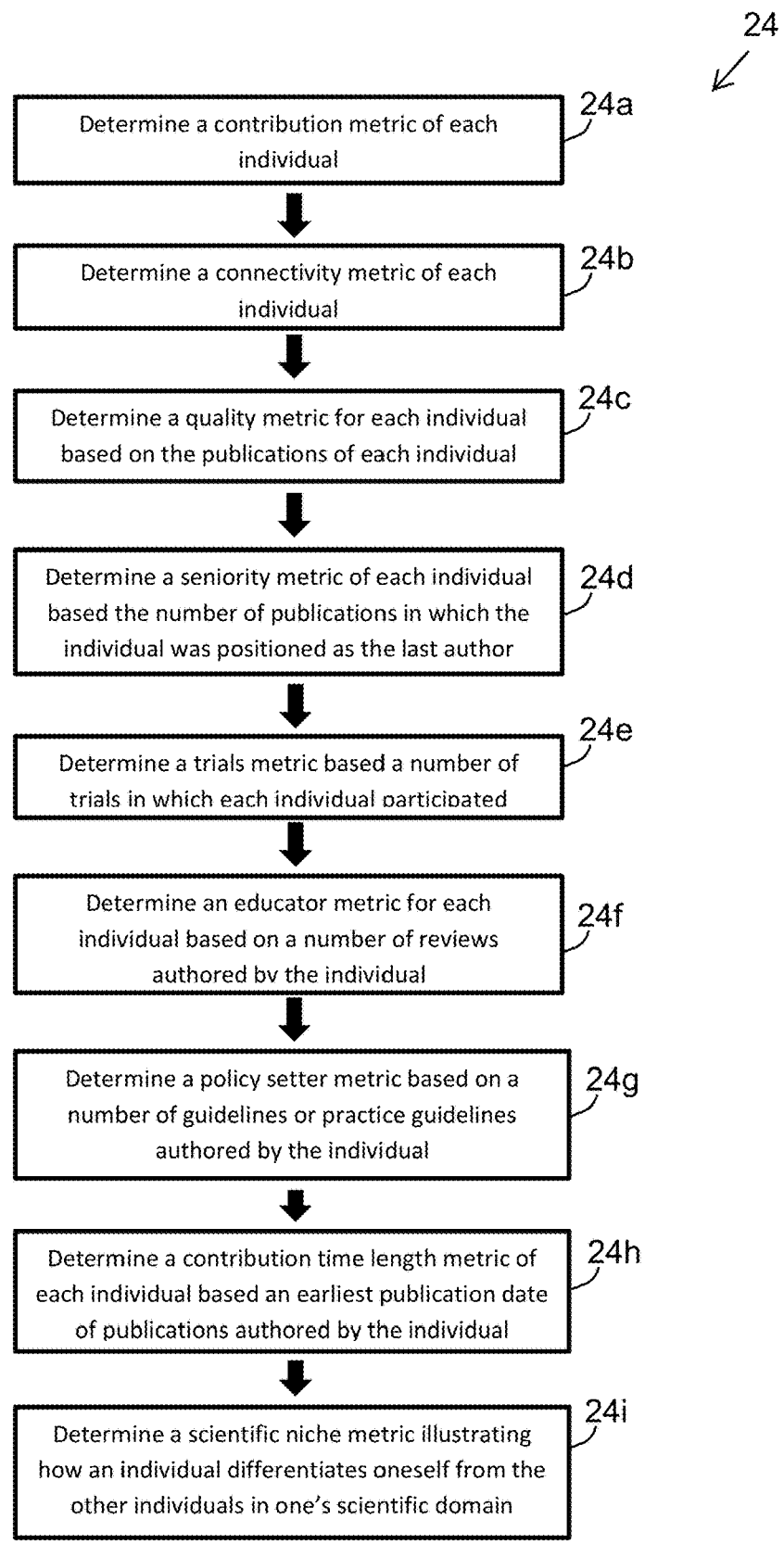
FIG. 1e shows substeps of a network augmentation technique in accordance with an embodiment of the present invention.

Method 10 further includes a network augmentation step 24. Step 24 includes enriching the entities and their relationships available in the primary data sources by adding properties to entities in the network that can be derived from the network and its characteristics. Each entity is defined by a node an entity's direct network is defined by the other nodes that are directly linked to the entity by a respective edge. As shown in FIG. 1e, for each of the entities stored in graph database 50, each entity's direct network is augmented by supplemental information including at least one supplemental metric in at least one of substeps 24a to 24g and stored in graph database 50 to generate the explorable network as described below. Supplemental information 24a to 24g is stored as node properties in graph database 50. The exemplary graph database, Neo4J, which is mentioned below, supports the property graph model and therefore nodes and edges/links can have properties. Other graph databases including such functionality can also be used.

A first substep 24a includes determining a contribution metric of each individual in graph database 50. The contribution metric of an individual is the number of publications published by the individual in graph database 50.

A second substep 24b includes determining a connectivity metric of each individual in graph database 50. The connectivity metric of an individual is the number of direct connections with other individuals through collaborations on a scientific publication or participation as an investigator in the same clinical trial. The connectivity metric of a researcher is a social network analysis metric, i.e., degree centrality.

A third substep 24c includes determining a quality metric for each individual based on the publications of each individual in graph database 50. The quality metric is calculated based on the number of citations acquired through the publications of the individual.

A fourth substep 24d includes determining a seniority metric of each individual in graph database 50. The seniority metric of an individual is the number of publications in which the individual was positioned as the last author.

A fifth substep 24e includes determining a trials metric of each individual in graph database 50. The trials metric is calculated based a number of trials in which each individual in graph database 50 participated as an investigator. Trials metrics are calculated mutatis mutandis.

A sixth substep 24f includes determining an educator metric for each individual in graph database 50. The educator metric for an individual is determined by number of reviews authored by the individual. In one preferred embodiment, the number of reviews is determined based on publication types provided by PubMed.

A seventh substep 24g includes determining a policy setter metric for each individual in graph database 50. The policy setter metric for an individual is determined by number of guidelines or practice guidelines authored by the individual. In one preferred embodiment, the number of guidelines or practice guidelines is determined based on publication types provided by PubMed.

An eighth substep 24h includes determining a contribution time length metric of each individual in graph database 50. The contribution time length metric of an individual is determined by an earliest publication date of publications authored by the individual.

A ninth sub step 24i includes determining an expertise metric of each individual in graph database 50 with respect to one or more specified topics. The expertise metric allows a better understanding of how an individual differentiates oneself from the other individuals in one's scientific domain. In one preferred embodiment, for every MeSH descriptor on which a researcher published its contribution to the individual's personal scientific niche, the expertise metric is calculated as follows:

$$\left(\frac{\text{Number of publications by author tagged with } \textit{MeSH} \text{ Descriptor}}{\text{Total number of publications by author}}\right) *$$

$$\log\left(\frac{\text{Total number of publications in database}}{\text{Total number of publications tagged with } \textit{MeSH} \text{ Descriptor in the database}}\right)$$

The expertise metric is stored as a property of an edge/link between the "individual node" and the node for the MeSH descriptor.

Step 24 may further include calculating other augmentation metrics such as, for example, a number of sites for clinical trials, members of an organizations, number of research papers contributed by organizations. In addition, publication and trial profiles for organizations are also calculated.

Method 10 further includes a knowledge inference step 24. Step 26 includes inferring knowledge from the existing relationships in the network. For example, Principal Investigators are not frequently disclosed in ClinicalTrials.gov for trials sponsored by a commercial company. However, when a link to the publication in which the results are disclosed is available for a trial, this additional piece of information is used to derive Principal Investigatorship based on the authors of this publication.

Figure 3:
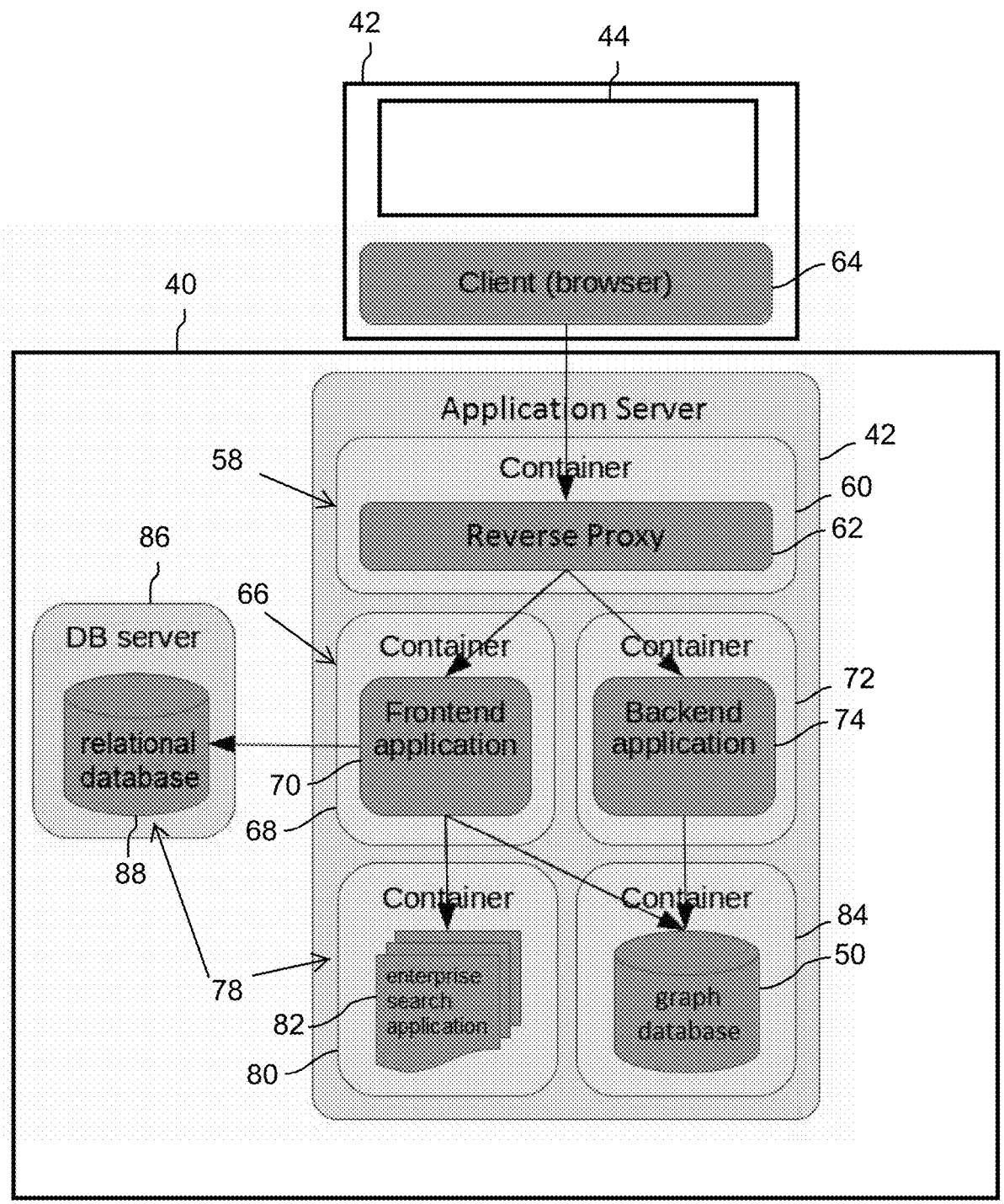
FIG. 3 schematically shows an embodiment of a computer system in accordance with an embodiment of the present invention.

FIG. 3 schematically shows an embodiment of a computer system 40 in accordance with an embodiment of the present invention. Computer system 40 includes a memory and a processor configured for performing the operations of steps 202 to 210 of method 200. Computer system 40 includes a KOL network exploration application server 42, which may in the form of a nontransitory computer readable medium stored on the hardware of computer system 40, configured for generating and displaying information from graph database 50 on GUIs of a display 44 of a client computer 46 in accordance with the method described below with respect to FIG. 17 and the GUI described below with respect to FIGS. 4a to 16.

Network exploration application server 42 has a layered architecture and includes a plurality of containers. Network exploration application server 42 includes a presentation layer 58 including a first container 60 including a reverse proxy 62, for example, Nginx: Reverse proxy, for interacting with a browser/client 64, which can be configured for supporting Chrome, IE11/Edge and iOS Safari. Reverse proxy 62 retrieves resources from a business layer 66 based on user inputs at browser/client 64 and directs the display of GUIs in response to the user inputs.

Business layer 66 includes a second container 68 including a frontend application 70, for example in the form of a Sinatra server, for providing content (e.g., HTML5 content), user management (state log/history), advanced search index via Solr. Business layer 66 also includes a third container 72 including a backend application 74, for example in the form of a Clojure application, configured to read data from graph database 50 of a database layer 78.

Database layer 78 includes a fourth container 80 of network exploration application server 42. Four container 80 including an enterprise search application 82, for example a Solr Search index, for search queries.

Database layer 78 also includes a fifth container 84 of network exploration application server 42. Fifth container 84 includes graph database 50, which in one preferred embodiment is for example a Neo4J graph database.

Computer system 40 also includes a database server 86, which in the embodiment shown in FIG. 3 is separate from network exploration application server 42, including an relational database 88, for example the relational database features of a Postgres SQL, for user state and history storage and caching of previous queries. Relational database 86 forms part of database layer 78.

Figure 4A:
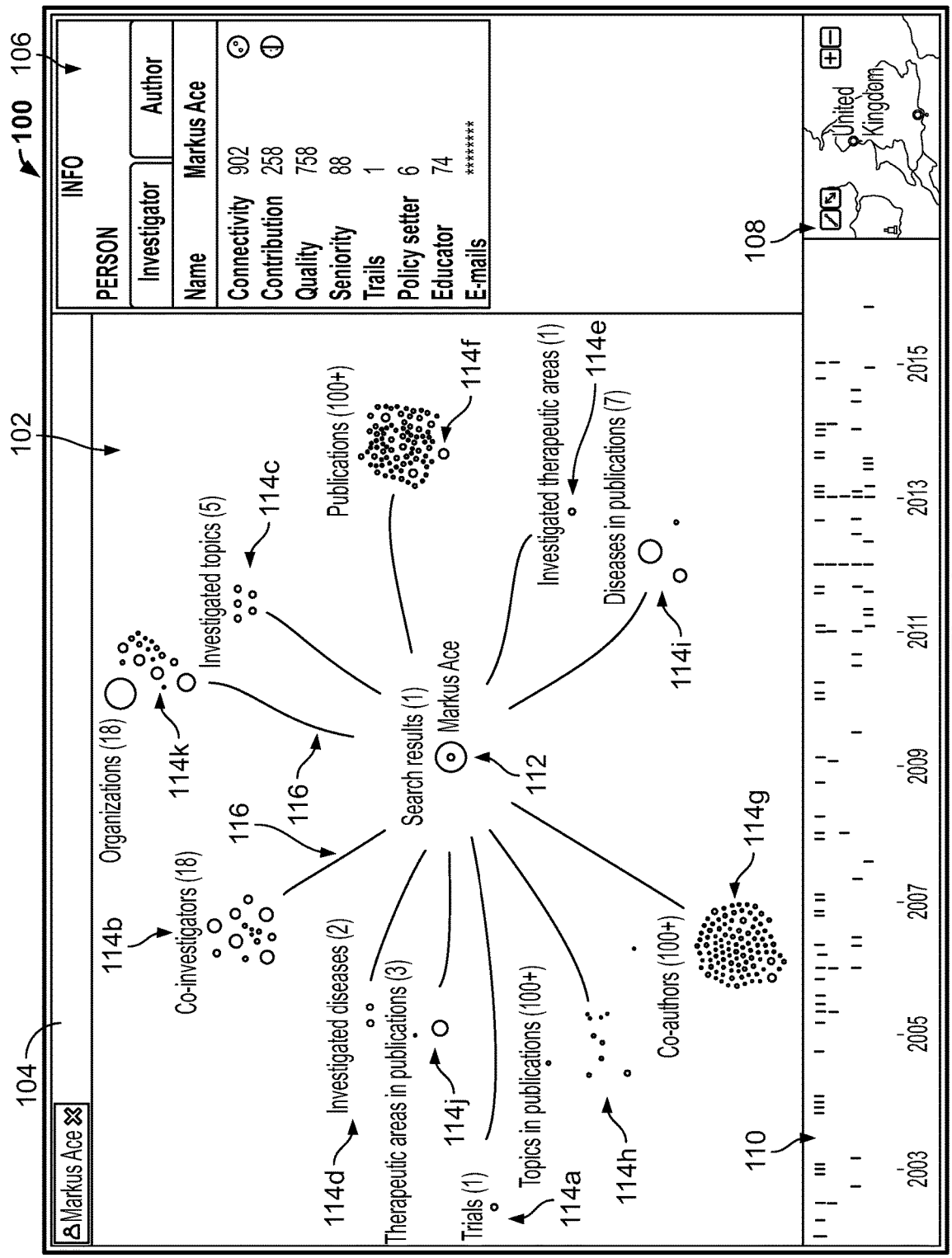
FIGS. 4a to 16 show examples of a network exploration graphical user interface generated in accordance with an embodiment of the present invention.
Figure 4B:
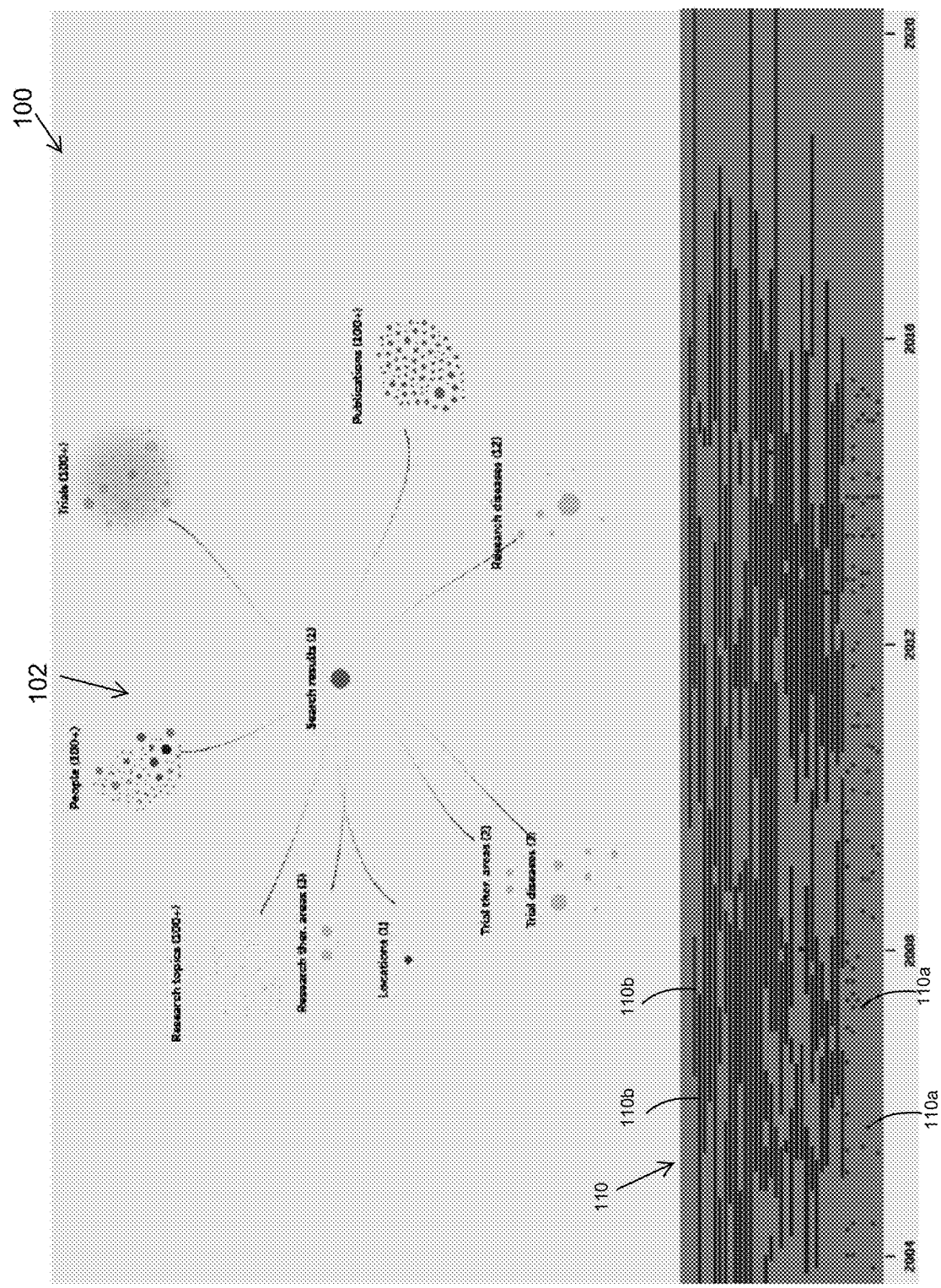

FIG. 4a shows a network exploration graphical user interface (GUI) 100 generated by network exploration application server 42 of computer system 40 on display 44 of client computer 46 shown in FIG. 3 in accordance with an embodiment of the present invention. GUI 100 allows a user of client computer 46 to explore and query the explorable network stored in graph database 50. GUI 100 includes a graph explorer section 102, an input section 104, a supplemental information section 106, a geographic section 108 and a timeline section 110. In response to an input by a user of client computer 42 into search input section 104, via an input device such as a keyboard, mouse and/or touchscreen for example, network exploration application server 42 generates corresponding information in graph explorer section 102, a side information section 106, a geographic section 108 and a timeline section 110.

A user may input on or more entities into search input section 104 by entering one or more search terms into search input section 104 and selecting one of the entity results generated in search input section 104 by the search terms. The entity results may each include a single entity or a grouping of a plurality of entities. More specifically, in response to an input of information by a user of client computer 42 into search input section 104, a code running in the client 64, for example a JavaScript code, makes a representational state transfer (REST) call that is dispatched by reverse proxy 62 to the frontend application 70. Frontend application 70 consults the enterprise search application 82 to map the user's input to the name of entities in the graph database 50 (again through REST). This information is fed back to the end user on GUI 100 via a dropdown list of potential entities or entity groups matching this input. In respect to the user's subsequent selection of an entity or entity group from the generated dropdown list, a call, for example an Asynchronous JavaScript and XML (AJAX) call, is sent by reverse proxy 62 to the backend application 74. The AJAX call first checks the database server 86 to determine if this selected entity or entity group has been previously queried and is therefore cached in database 88. If this is the case, the results of this user's query, which is stored in database 88 for example as a JavaScript Object Notation (JSON) document, are returned to the client 64 to enable the client to render the results of the user's query in the different sections of 102, 106, 108, 110 of GUI 100. If the user's query is not cached in the relational database 88, the backend application 74 consults the graph database 50, transforms these results and sends them back to the client 64, which renders the results of the user's query in the different sections of 102, 106, 108, 110 of GUI 100.

In the example shown in FIG. 4a, a user has input a single entity, more specifically an individual's name, via input section 104. In response to the input, search application 82 searches graph database 50 and generates a partial view of the explorable network stored in graph database 50 in graph explorer section 102. The partial view is centered on the input entity and illustrates the input entity and entities or entity groups directly linked to the input entity. A center node icon 112 represents the input entity—in this example, the individual—and a plurality of outer node icons 114a to 114k, which each represent an entity or an entity group linked to the input entity in the explorable network stored in graph database 50, centered around center node icon 112 and directly connected to center node icon 112 by links 116. Each node icon is either a cloud representing an entity group or a node representing a single entity. Each cloud includes a plurality of nodes of a single entity group. Each node icon 114a to 114k is labeled with the title of the entity group and a number of entities within the entity group. Each of node entities 114a to 114d and 114f to 114k is a cloud including a plurality of nodes in a number equal to the entities within the group. Both the entire collection of nodes in the cloud as well as each individual node in the cloud are selectable. In this embodiment, the cloud is selected by clicking on the caption of the cloud and a node within a cloud is selected by clicking on the node itself.

The nodes are sized differently to indicate varying importance of each entity. Opacity is also used to differentiate the nodes within a cloud. Size and opacity are defined differently for every kind of group of nodes in the graph explorer section 102. For example, for co-author nodes and co-investigator nodes, the size of each node represent the number of direct connections with other researchers through collaborations on a scientific publication or clinical trial and opacity of each node represents the number of articles published by a co-author or the number of trials participated in by a co-investigator. For publication nodes, only the size of the nodes varies and according to the number of citations of these publications). For clinical trial nodes, the size of each node represents the enrollment if the study is an interventional study, otherwise the size is minimal, and the opacity represents the number of sites for the clinical trial. For organization nodes, the size of each organization node represents the number of individuals affiliated with the organization and the opacity represents the number of publications issued by the organization. A publication is considered as being issued by an organization is if the organization is mentioned as being affiliated with of one of the authors of the publication, including as an employer or a sponsor of the individual's research, or when the individual acts as an advisor to the organization. For subject matter nodes, the size of each node represents the number of publications for a topic, disease or therapeutic area and the opacity represents the number of individuals (authors or investigators) active on a topic, disease or therapeutic area.

Node icons 114a to 114e relate to clinical trial information. A first node icon 114a is a single node labeled with the title "trials" and number "1" indicates that the input individual is listed as a researcher for one clinical trial.

A second node icon 114b is a cloud labeled with the title "co-investigators" and number "18" represents the eighteen different individuals that are identified as being co-investigators with the input individual in the one clinical trial.

A third node icon 114c is a cloud labeled with the title "investigated topics" and number "5" indicates that the one clinical trial in which the input individual is listed as a researcher relates to five topics.

A fourth node icon 114d is a cloud labeled with the title "investigated diseases" and number "2" indicates that the one clinical trial in which the input individual is listed as a researcher relates to two diseases.

A fifth node icon 114e is a cloud labeled with the title "investigated therapeutic areas" and number "1" indicates that the one clinical trial in which the input individual is listed as a researcher relates to one therapeutic area.

Node icons 114f to 114j relate to publication information. A sixth node icon 114f is a cloud labeled with the title "publications" and number "100+" indicates that the input individual is listed as an author for more than a hundred different publications.

A seventh node icon 114g is a cloud labeled with the title "co-authors" and number "100+" indicates that the more than a hundred different individuals that are identified as being co-authors with the input individual in the publications.

An eighth node icon 114h is a cloud labeled with the title "topics in publications" and number "100+" indicates that the publications in which the input individual is listed as author relate to more than a hundred topics.

A ninth node icon 114i is a cloud labeled with the title "diseases in publications" and number "7" indicates that the publications in which the input individual is listed as author relate to seven diseases.

A tenth node icon 114j is a cloud labeled with the title "therapeutic areas in publications" and number "3" indicates that the publications in which the input individual is listed as author relate to three therapeutic areas.

An eleventh node icon 114k is related to both the publication information and the clinical trial information. Node icon 114k is a cloud labeled with the title "organizations" and number "18" indicates that the publications in which the input individual is listed as author and the one clinical trial in which the input individual is listed as a researcher are linked to eighteen different organizations.

In addition to the display of the partial view of the network, a geographic map including icons depicting the locations of organizations represented by the partial view is generated in geographic information section 108. Geolocation information is stored in the graph database as "location nodes". The geolocation of "organization nodes" is stored as a link to such a "location node". In the example shown in FIG. 4a, geographic information section 108 is centered on the United Kingdom; however, a mouse or touchscreen can be used to examine other locations to determine whether an organization or individual is professionally located in a region of interest.

In response to a user selection of center node icon 112 or one of node icons 114a to 114k in graph explorer section 102, supplemental information for the entity of center node icon 112 or the entities within the selected node icon 114a to 114k is generated in supplemental information section 106. This supplemental information is loaded together with the information returned to the client in response to user input. Displaying the appropriate supplemental information is dealt with at the client side 64. The web browser, has this information as part of the web page (DOM) and the javascript code describes the web browser how and when to render the information and when to render it. In the example shown in FIG. 4a, center node icon 112 is selected in graph explorer section 102, and in response, exploration application server 42 of computer system 40 generates supplemental information linked to the input individual corresponding in supplemental information section 106 on GUI 100. In this embodiment, the supplemental information displayed for individual represented by center node icon 112 are the connectivity metric, contribution metric, quality metric, seniority metric, trials metric, policy setter metric, educator metric, as described above with respect to step 24, along with the contact email of the individual. Display of these metrics allows a user to quickly review a number of KOL-related metrics in a single location.

Figure 5:
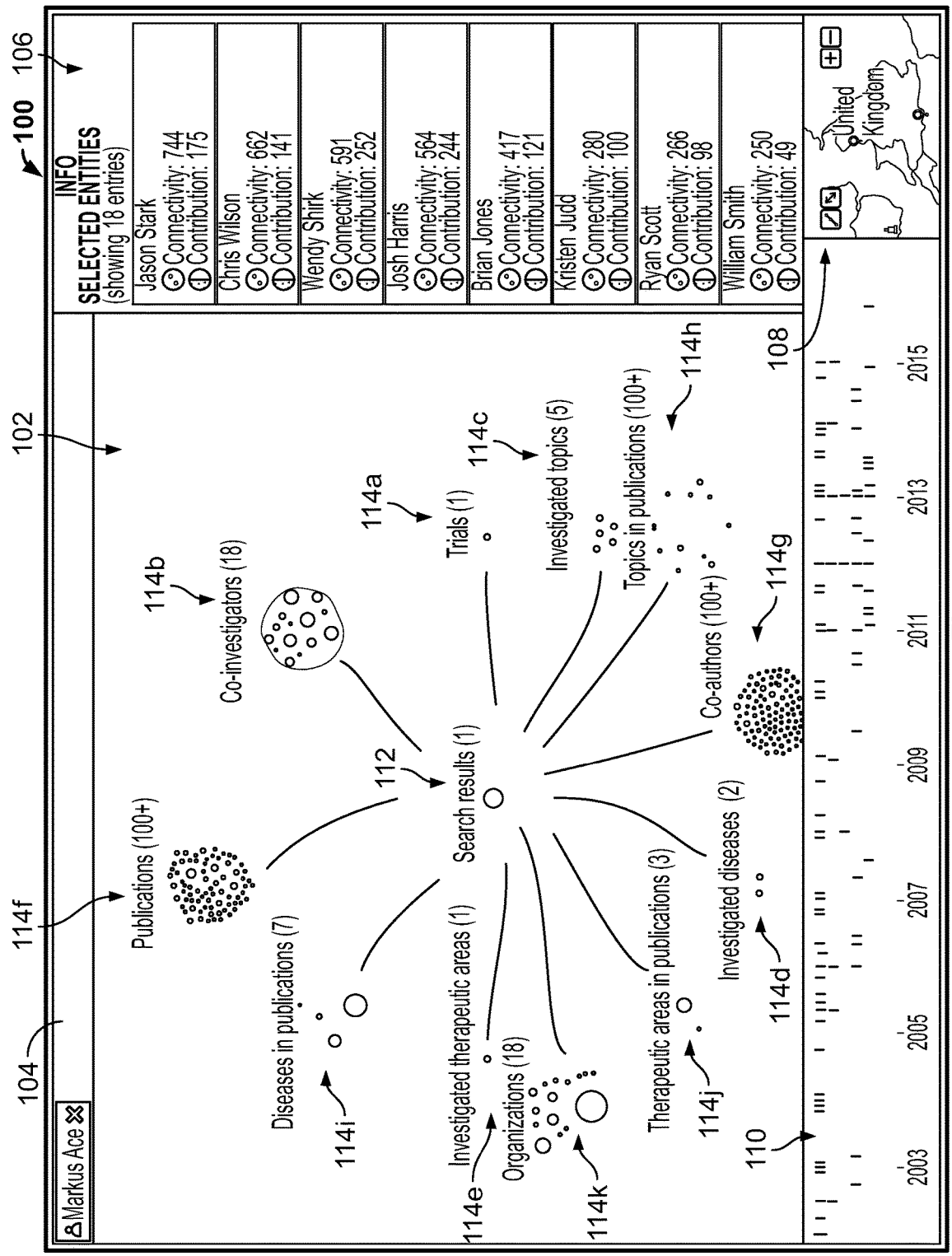

Timeline section 110 displays all time information. Another example of timeline section 110 is shown more clearly in FIG. 4b., Timeline section 100 displays time related information on two types of entities currently being shown the graph explorer section 102: (1) for publications the date of publication is indicated as a dot 111a; (2) trials are depicted as lines 111b indicating the overall duration from start until completion date. The currently selected trial(s)/publications(s) are indicated in a dots or lines. FIG. 5 shows GUI 100 with an outer node icon selected. In response to a user selection of one of the node icons 114a to 114k in graph explorer section 102, each of the entities, here co-investigators, within the selected node icon 114a to 114k are generated in supplemental information section 106 along with corresponding supplemental information for each co-investigator. In the example shown in FIG. 5, second node icon 114b is selected in graph explorer section 102, and in response, exploration application server 42 of computer system 40 generates supplemental information for each of the eighteen individuals identified as being co-investigators with the input individual in supplemental information section 106. Although only eight different individuals are represented in supplemental information section 106 in FIG. 5, a user can scroll down to review the information of the additional ten individuals. In this embodiment, the supplemental information displayed for each co-investigator is the connectivity metric and contribution metric. The co-investigators are ordered by the connectivity metric in descending order in supplemental information section 106 such that the individual with the greatest number of direct connections with other individuals through collaborations on a scientific publication or participation as an investigator in the same clinical trial is listed at the top of the supplemental information section 106, allowing the user to identify which co-investigator linked to the input individual is most identifiable as a KOL. Selection of node icon 114g results in a similar operation, generating authors within the group corresponding to the selected node icon in supplemental information section 106, along with the corresponding connectivity metric and contribution metric for each author.

Figure 6:
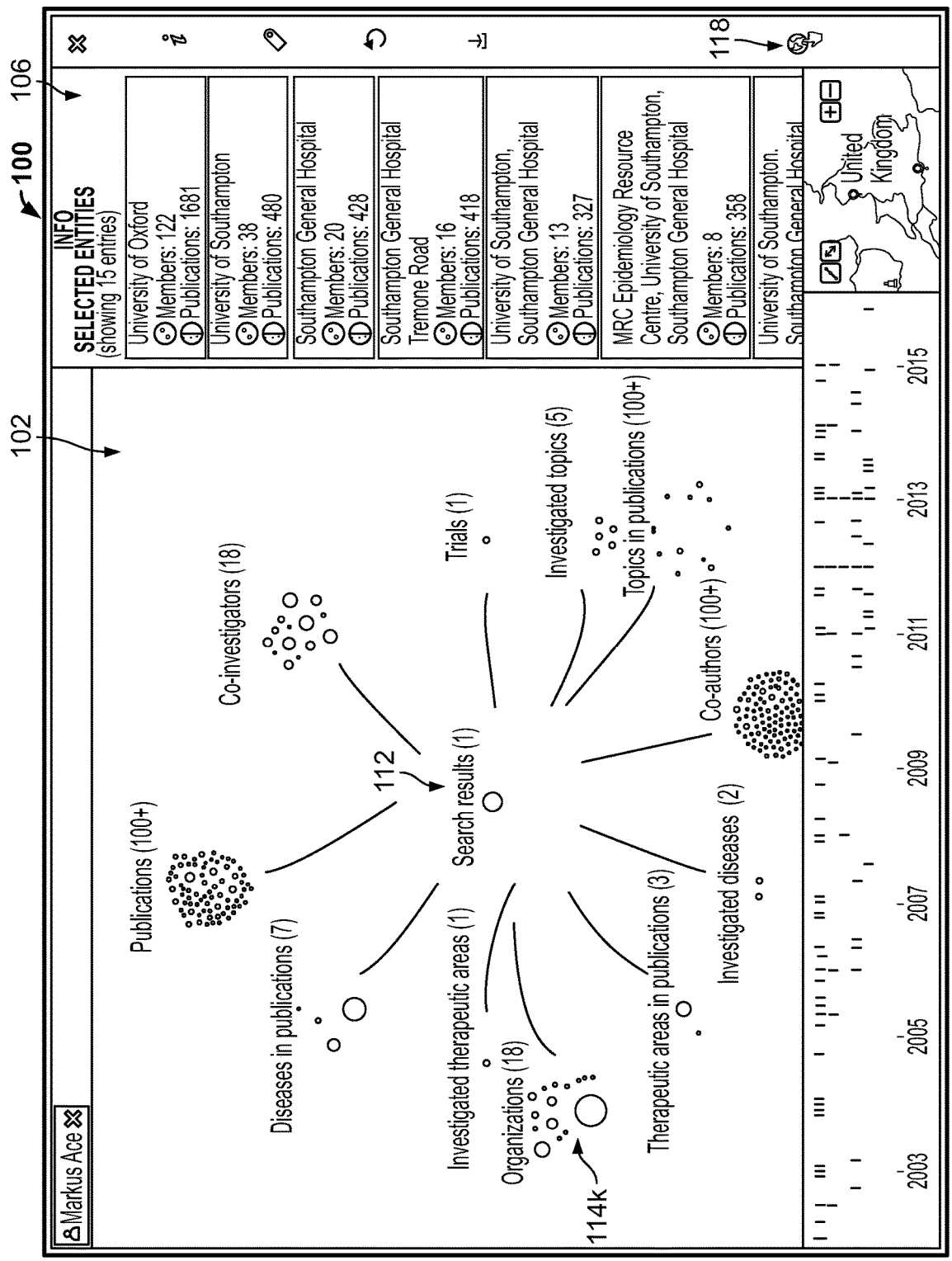

FIG. 6 shows GUI 100 with another outer node icon selected. In the example shown in FIG. 6, node icon 114k is selected in graph explorer section 102, and in response, exploration application server 42 of computer system 40 generates supplemental information for each of the eighteen organizations identified as being linked to the input individual in supplemental information section 106. Although only seven different organizations are represented in supplemental information section 106 in FIG. 4a, a user can scroll down to review the information of the additional eleven organizations. In this embodiment, the supplemental information displayed for each organization is the number of members, i.e., individuals identified as researchers and authors, associated with the organization in the data set and the number of publications in the data set associated with the organization. Because graph database 50 is restricted to a limited number of diseases in steps 14, 16, this metric gives provides guidance on the importance of these organizations with respect to the diseases delimited in graph database 50 in steps 14, 16.

Figure 7:
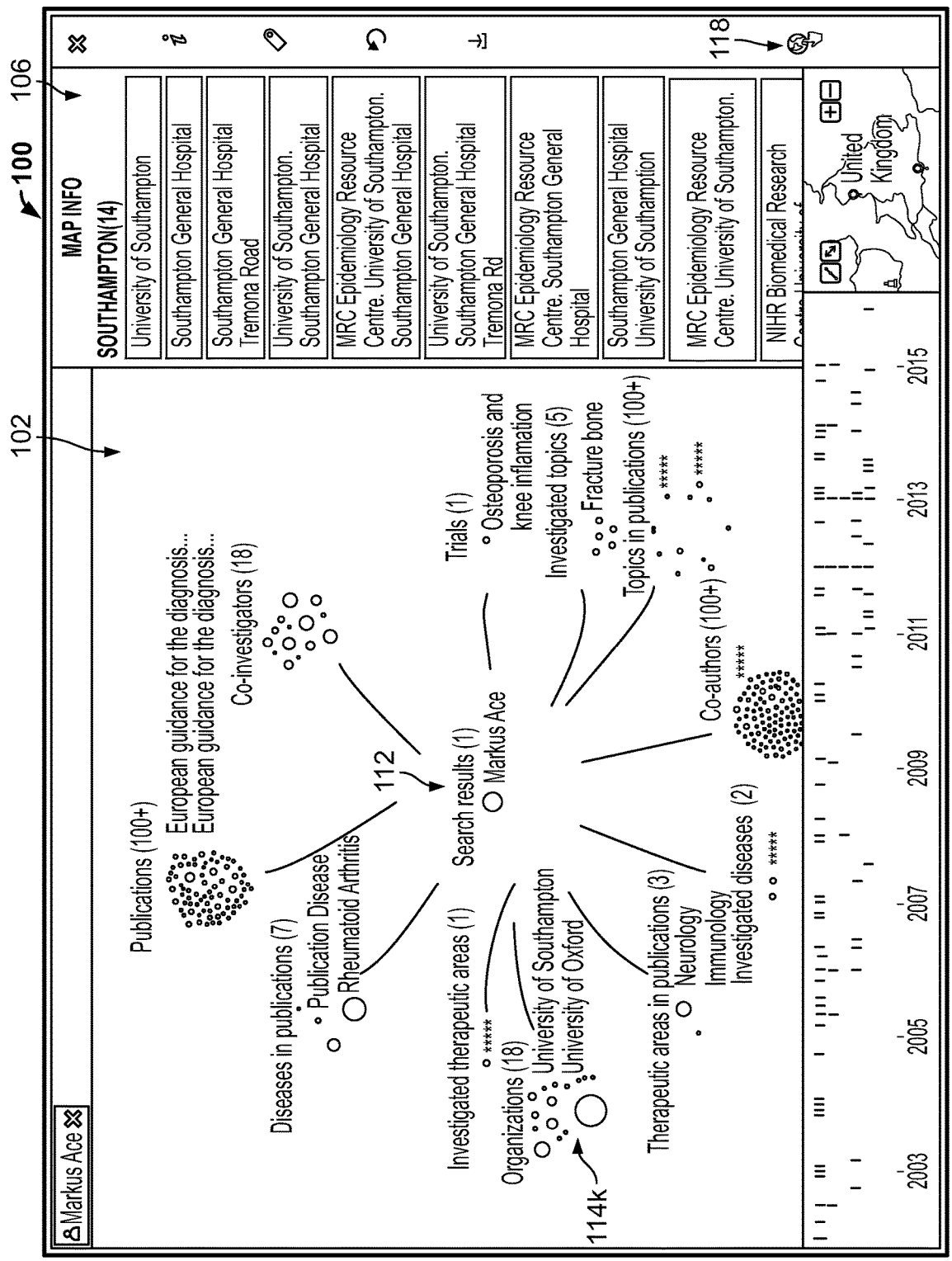

The organizations are also shown geographic section 108 on the displayed map. The geographic section 108 illustrates with a number beside an icon representing the city Southampton that seventeen of the organizations are located in or around Southampton. Geographic section 108 also includes a geographic icon 118 that is selectable to alter the information displayed in information section 106. As shown in FIG. 7, upon selection of geographic icon 118, the list of organizations in Southampton is displayed in the information section 106. Additionally, scrolling down in information section 106 would display three organizations for Oxford and one organization for UK.

Figure 8:
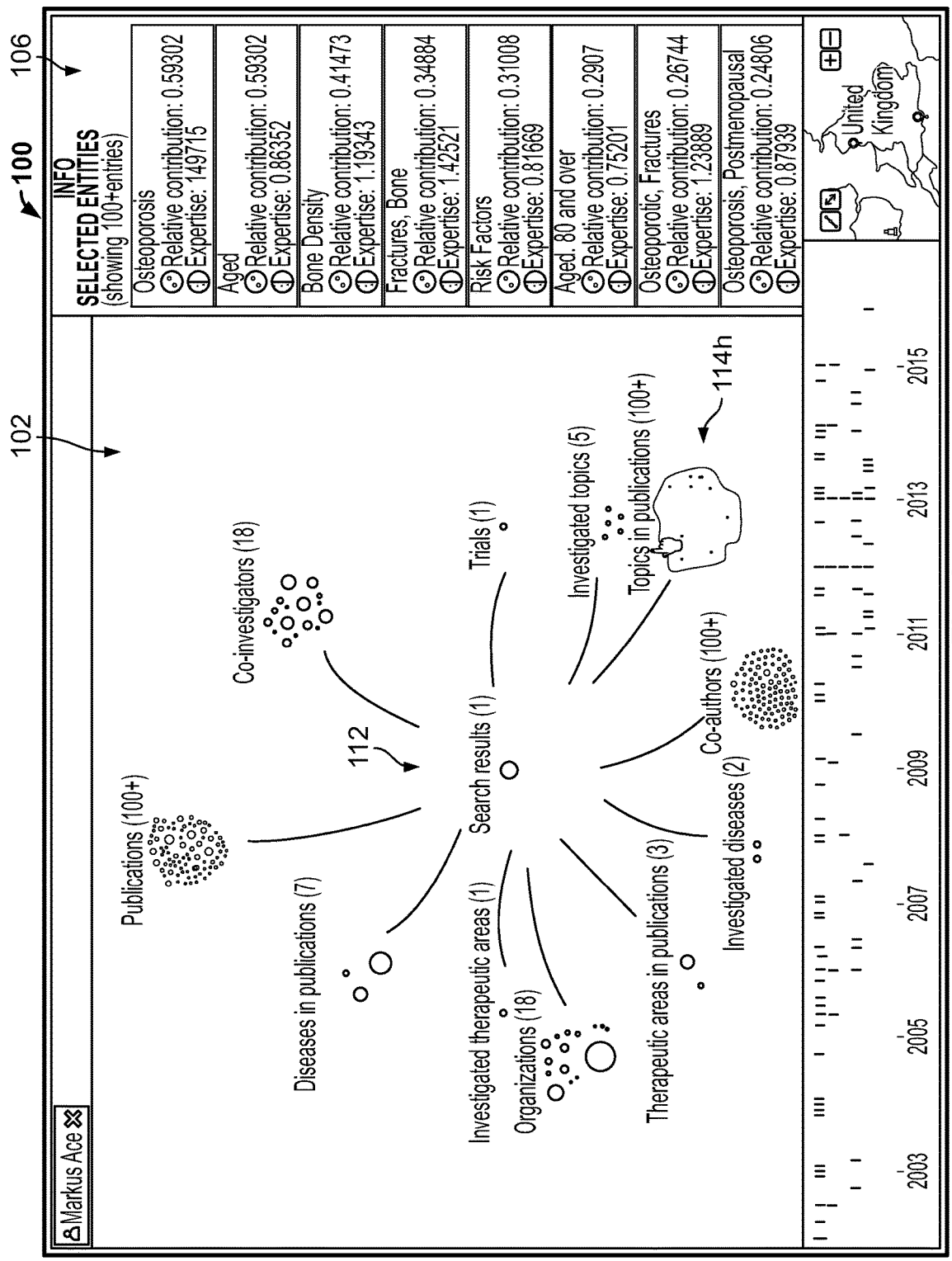

FIG. 8 shows GUI 100 with another outer node icon selected. In the example shown in FIG. 7, node icon 114h is selected in graph explorer section 102, and in response, exploration application server 42 of computer system 40 generates entities, here topics, within the group corresponding to the selected node icon and supplemental information for each of the hundred plus topics identified as being linked to the input individual in supplemental information section 106. In this embodiment, the supplemental information displayed for each topic is a relative contribution metric, calculated by dividing the number of publications of an author tagged with this MeSH Descriptor by the total number of publications by this author, quantifying the relative contribution of the input individual to the topic and an expertise metric, calculated in the manner described in step 24i, quantifying the expertise of the input individual with respect to the topic. Selection of node icon 114c results in a similar operation, generating topics within the group corresponding to the selected node icon and the corresponding relative contribution and expertise metrics for each of the five investigated clinical trial topics identified as being linked to the input individual in supplemental information section 106.

Figure 9:
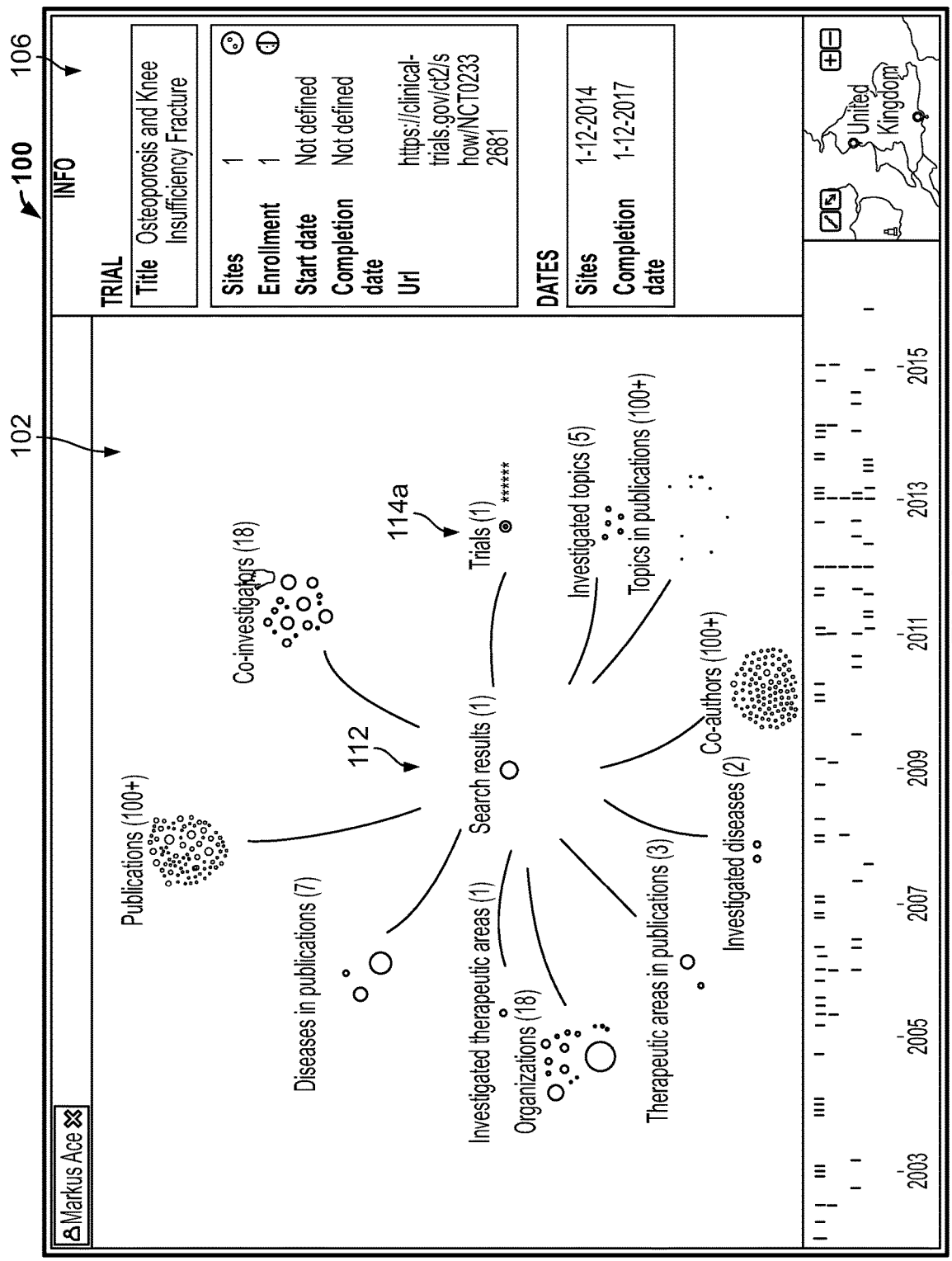

FIG. 9 shows GUI 100 with another outer node icon selected. In the example shown in FIG. 8, node icon 114a is selected in graph explorer section 102, and in response, exploration application server 42 of computer system 40 generates the sole entity, here one trial titled "Osteoporosis and Knee Insufficiency Fracture," within the group corresponding to the selected node icon and supplemental information for the trial. In this embodiment, the supplemental information displayed for the trial each topic is the number of sites, enrollment and the start and end dates.

Figure 10:
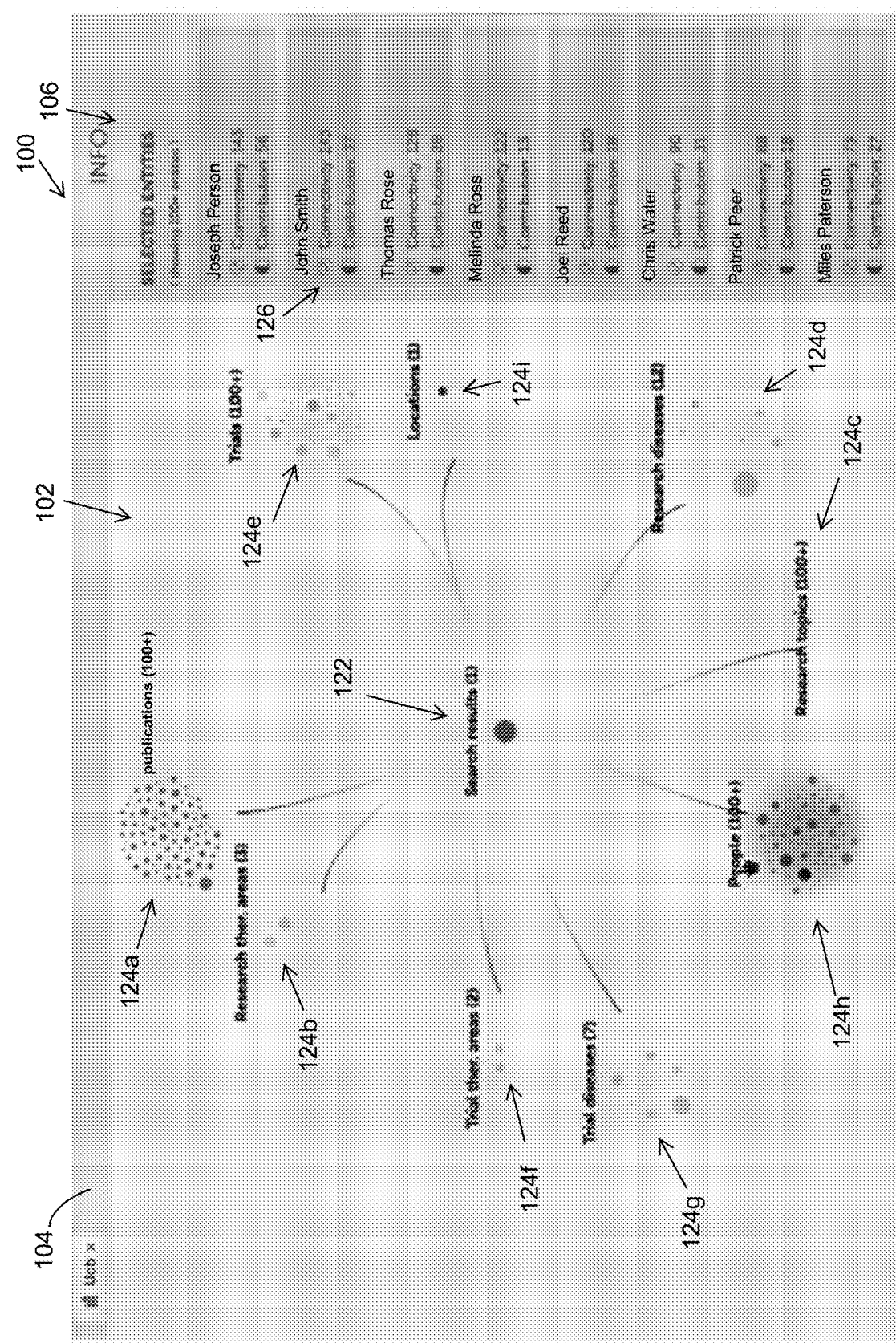

FIG. 10 shows GUI 100 with the organization UCB entered into input section 104. In response, network exploration application server 42 generates a new partial view of the explorable network in graph explorer section 102 illustrating entities directly linked to the input organization in graph database 50. More specifically, in response to an input of information by a user of client computer 42 into search input section 104, reverse proxy 62 retrieves information from database layer 78 via business layer 66 and modifies GUI 100 as instructed by business layer 66. In response to the inputs, reverse proxy 62 accesses database 50, and search application 82 via backend application 74 and frontend application 70 directs the modification of GUI 100 via reverse proxy 62.

A center node icon 122 represents the input organization and a plurality of outer node icons 124a to 124i, which represent entities directly linked to the input entity in graph database 50, centered around center node icon 122 and connected to center node icon 122 by links 126. Node icons 124a to 124d relate to publication information. A first node icon 124a is labeled with the title "publications" and number "100+" indicates that the input organization is linked with more than a hundred different publications. As similarly noted above, the link indicates that individuals working for the company have published over a hundred publications during their employment.

A second node icon 124b is labeled with the title "research therapeutic areas" and number "3" indicates that the publications in which at least one employee of the input organization is listed as author relate to three therapeutic areas.

A third node icon 124c is labeled with the title "research topics" and number "100+" indicates that the publications in which at least one employee of the input organization is listed as author relate to more than a hundred topics.

A fourth node icon 124d is labeled with the title "research diseases" and number "12" indicates that the publications in which at least one employee of the input organization is listed as author relate to twelve diseases Node icons 124e to 124g relate to clinical trial information. A fifth node icon 124e is labeled with the title "trials" and number "100+" indicates that the input organization is listed as an investigator for more than a hundred clinical trials.

A sixth node icon 124f is labeled with the title "trial therapeutic areas" and title "investigated therapeutic areas" and number "2" indicates that the clinical trials in which the input organization is an investigator relate to two therapeutic areas.

A seventh node icon 124g is labeled with the title "trial diseases" and number "7" indicates that the clinical trials in which the input organization is an investigator relate to seven diseases.

An eighth node icon 124h is labeled with the title "people" and number "100+" indicates that the input organization is linked to more than one hundred individuals in the publications and trials.

A ninth node icon 124i is labeled with the title "locations" and the number "1" indicates that the organization has a single location.

In the example shown in FIG. 10, node icon 124h is selected in graph explorer section 102, and in response, exploration application server 42 generates supplemental information linked to the individuals linked to the input organization in supplemental information section 106 on GUI 100. In this embodiment, the supplemental information displayed for each individual represented by node icon 124h are the connectivity metric and the contribution metric.

Any of the individuals listed in supplemental information section 106 are selectable to modify graph explorer section 102. Each individual and the individual's corresponding information are provided in a selectable subsection 126 of supplemental information section 106, with eight subsections 126 being shown in FIG. 10. Upon selection of the subsection 126 of supplemental information section 106 specifically labeled in FIG. 10 related to the individual John Smith, exploration application server 42 of computer system 40 modifies graph explorer section 102 to generate a new partial view of the explorable network stored in graph database 50 on GUI 100, as shown in FIG. 11, with the selected individual, John Smith being represented by a center node icon 132.

Figure 11:
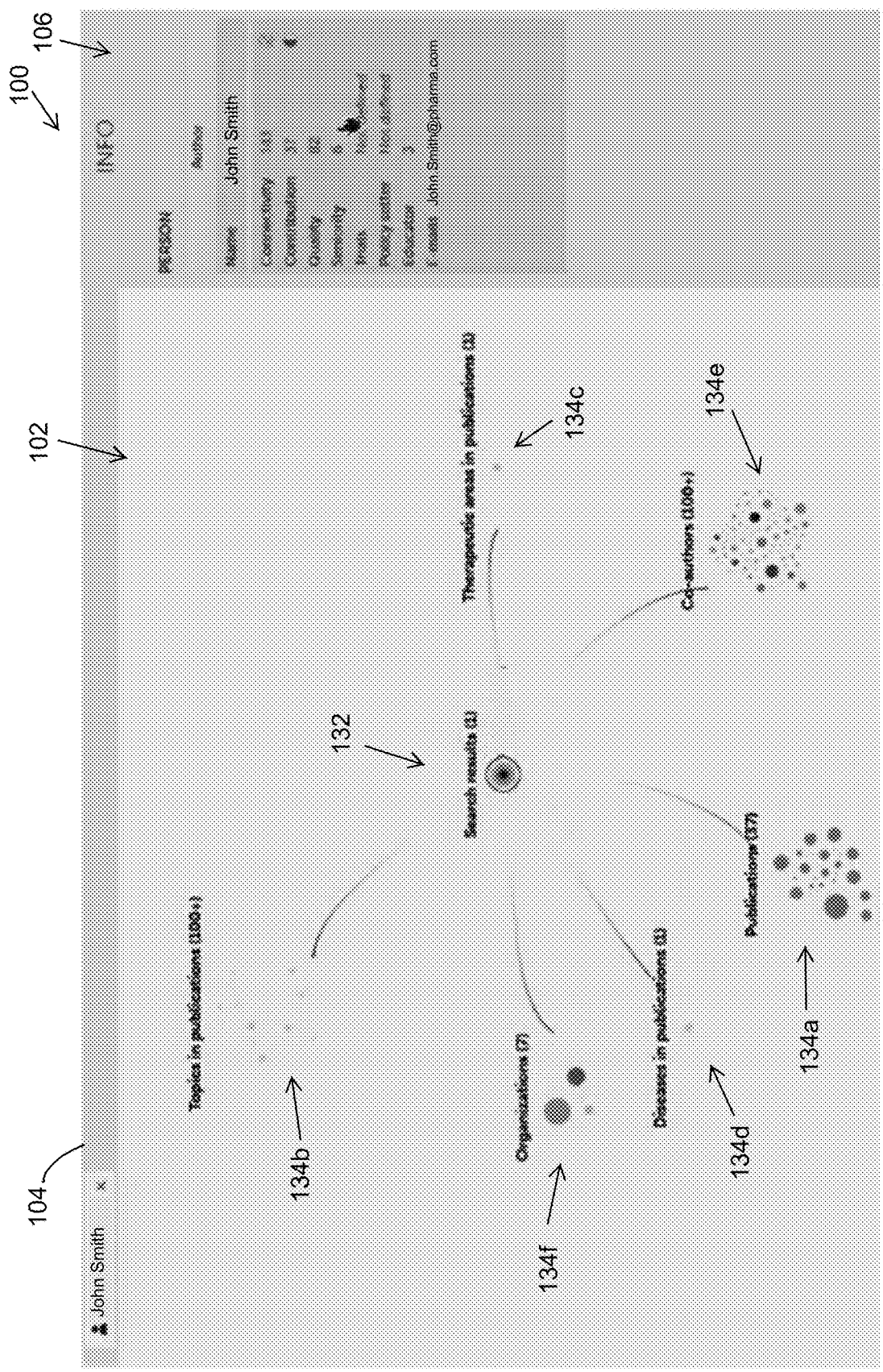

As shown in FIG. 11, John Smith is the author of a thirty-seven different publications, but has not been involved in a clinical trial. Accordingly, node icons 134a to 134f are generated in relation to the publications that John Smith authored, but no node icons are generated for clinical trial information.

Figure 12:
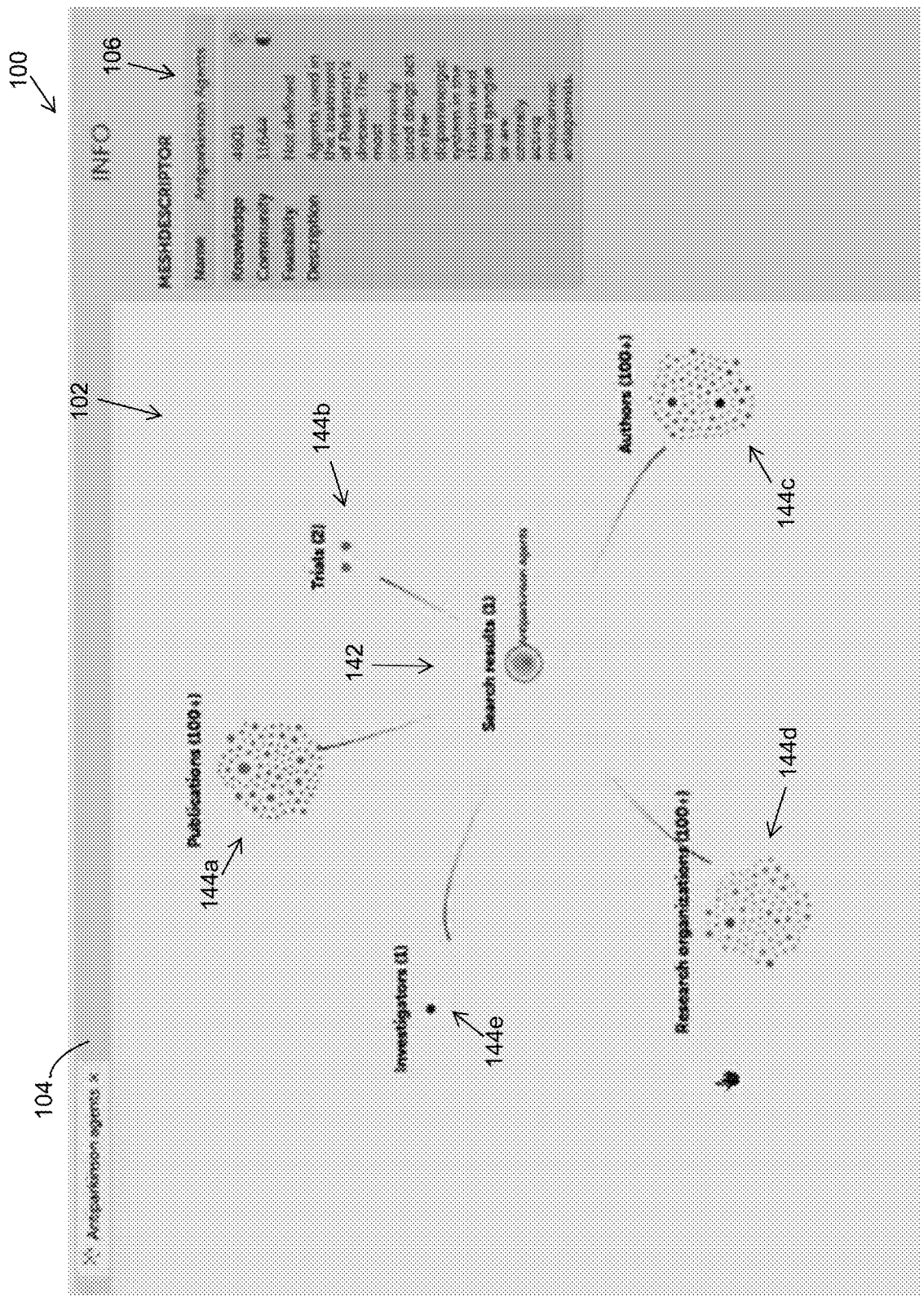

FIG. 12 shows a topic being entered via input section 104 to generate a partial view of the explorable network centered around the input topic in graph explorer section 102. In this example, Antiparkinson agents is the input topic and a center node icon 142 represents this topic. Outer node icons 144a to 144e are generated around center node icon 142. A first outer node icon 144a represents the publications directly linked to Antiparkinson agents in graph database 50, a second outer node icon 144b represents the clinical trials directly linked to Antiparkinson agents in graph database 50, a third outer node icon 144c represents authors of publications directly linked to Antiparkinson agents in graph database 50, a fourth outer node icon 144d represent research organizations directly linked to Antiparkinson agents in graph database 50 and a fifth outer node icon 144e represents a clinical trial investigator directly linked to Antiparkinson agents in graph database 50. Because center node icon 142 has been selected by the user, supplemental information section 106 displays supplemental information for Antiparkinson agents. The supplemental information includes a knowledge metric, a community metric and a feasibility metric, along with a description of Antiparkinson agents. The knowledge metric represents the number of publications in the entire database that are tagged with this MeSH descriptor, the community metric represents the number of authors and investigators linked to publications and trials that are tagged with this MeSH descriptor, and the feasibility metric represents the number of trials in the entire database that are tagged with this MeSH descriptor.

Figure 13:
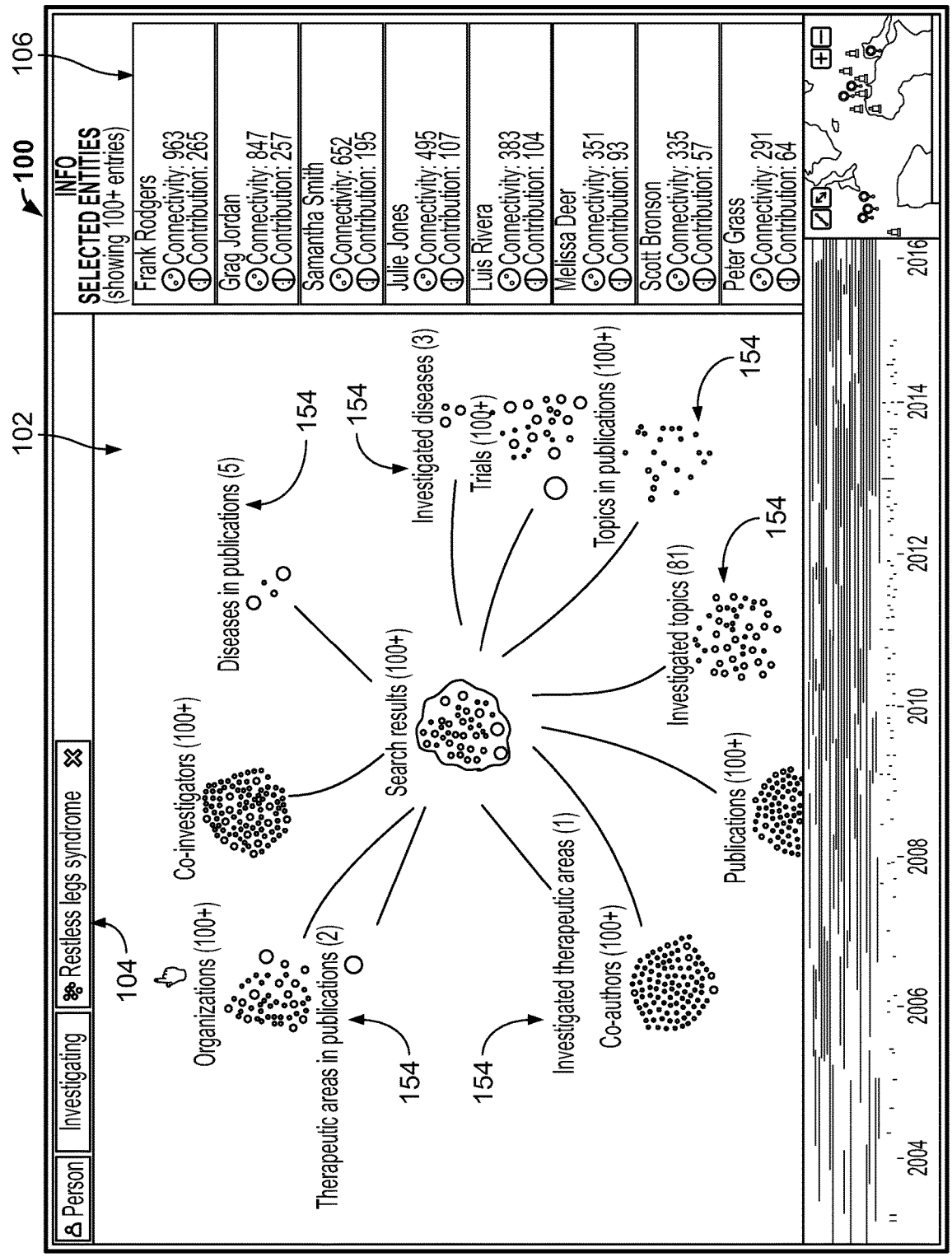

FIG. 13 shows another manner in which GUI 100 is configured for receiving user inputs. As shown in FIG. 13, the user input "person investigating Restless legs syndrome" in input section 104 and exploration application server 42 of computer system 40 searches graph database 50 to identify each individual linked with clinical trials related to Restless legs syndrome and modifies graph explorer section 102 to generate a different partial view of the explorable network on GUI 100. The partial view generated in graph explorer section 102 in FIG. 13 includes a center node icon 152 including individuals linked to trials linked to Restless legs syndrome in graph database 50. As indicated by the label in FIG. 13, more than a hundred individuals are included in this group. The individuals with the highest connectivity metrics are generated in supplemental information section 106 due to the selection of center node icon 152, allowing a user to easily generate a list of the KOLs for Restless legs syndrome on GUI 100. Similar to the examples described above, a plurality of outer node icons 154 are generated in graph explorer section 102 based on the links between the investigators represented by center node icon 152 and the other entities in graph database 50.

Figure 14:
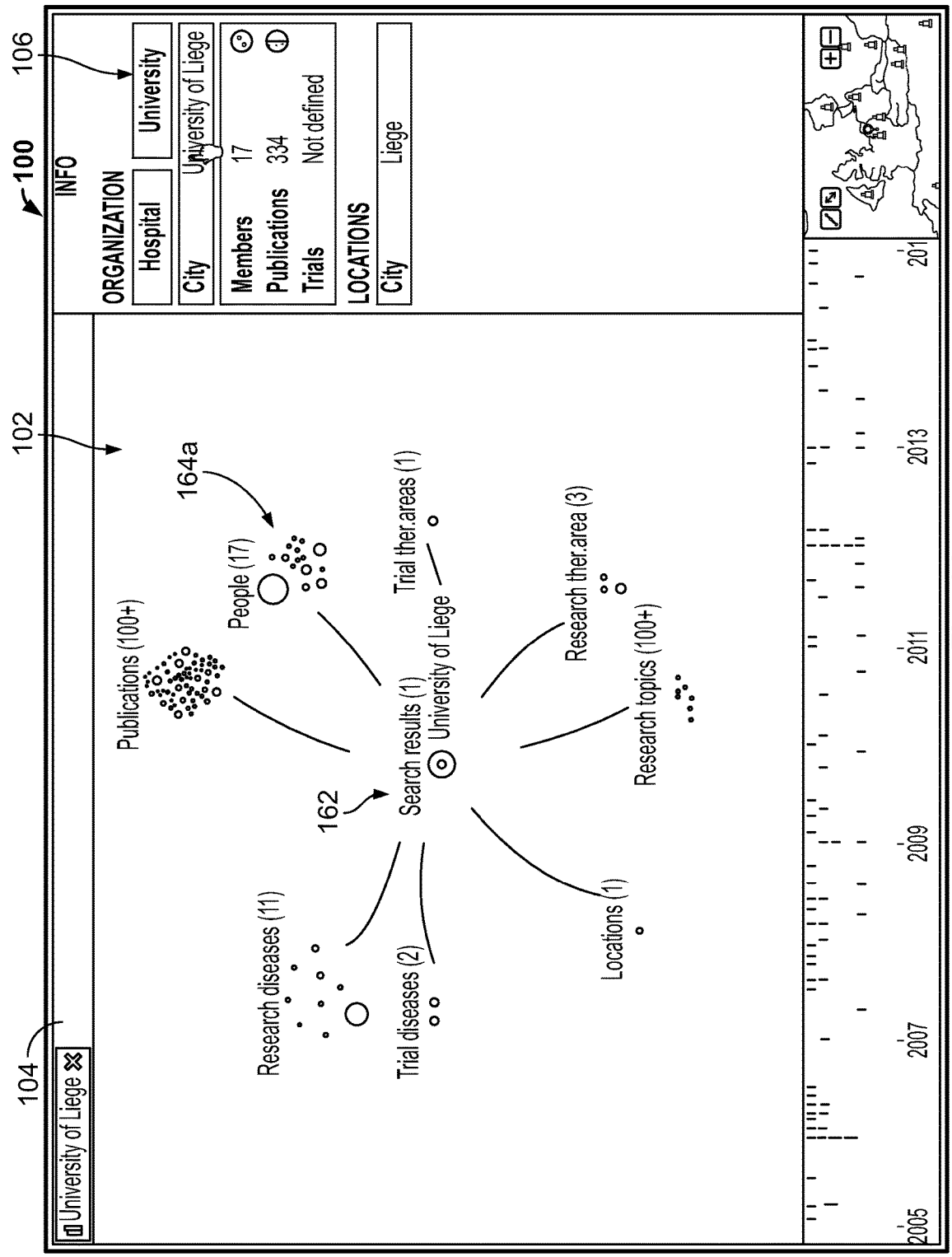
Figure 15:
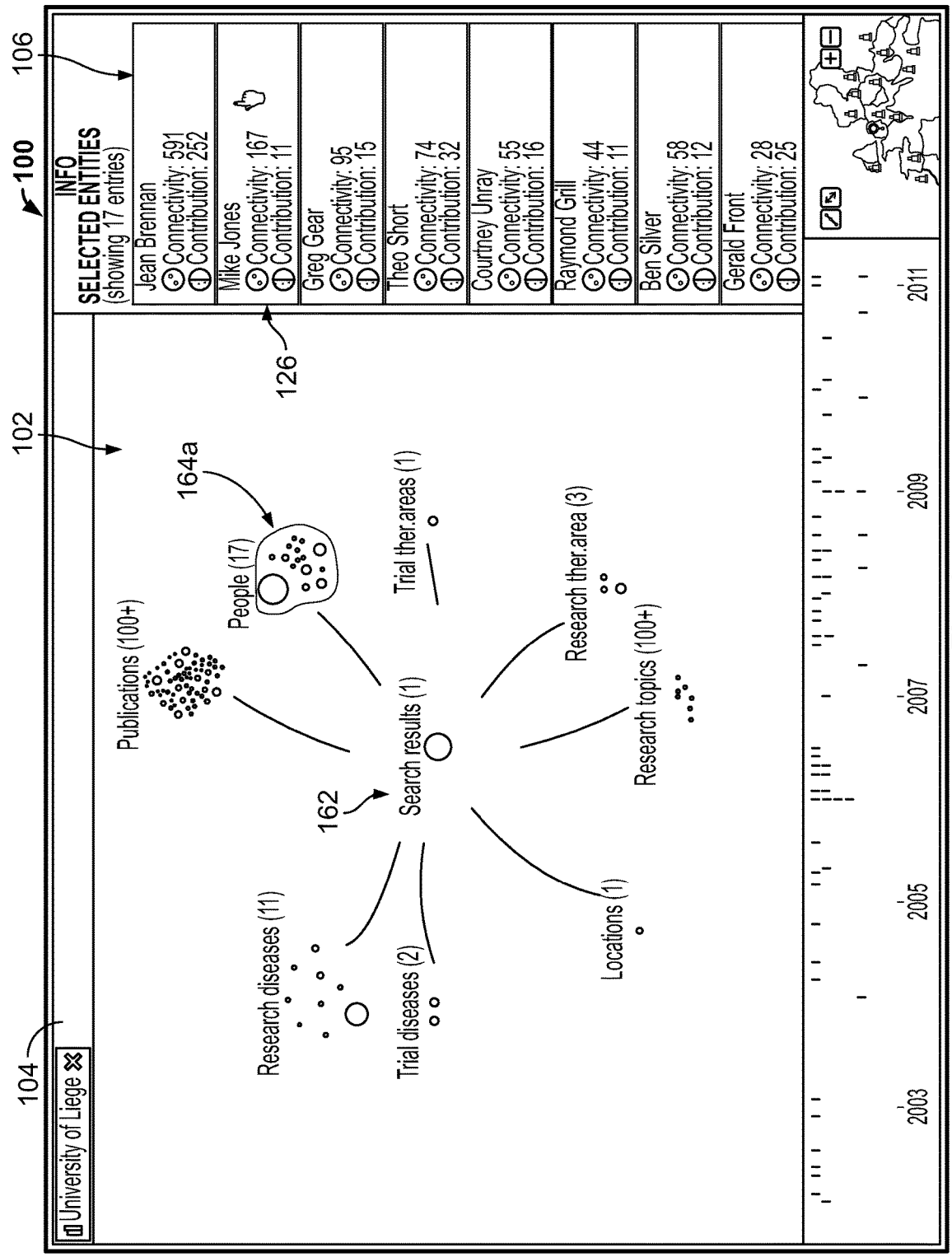
Figure 16:
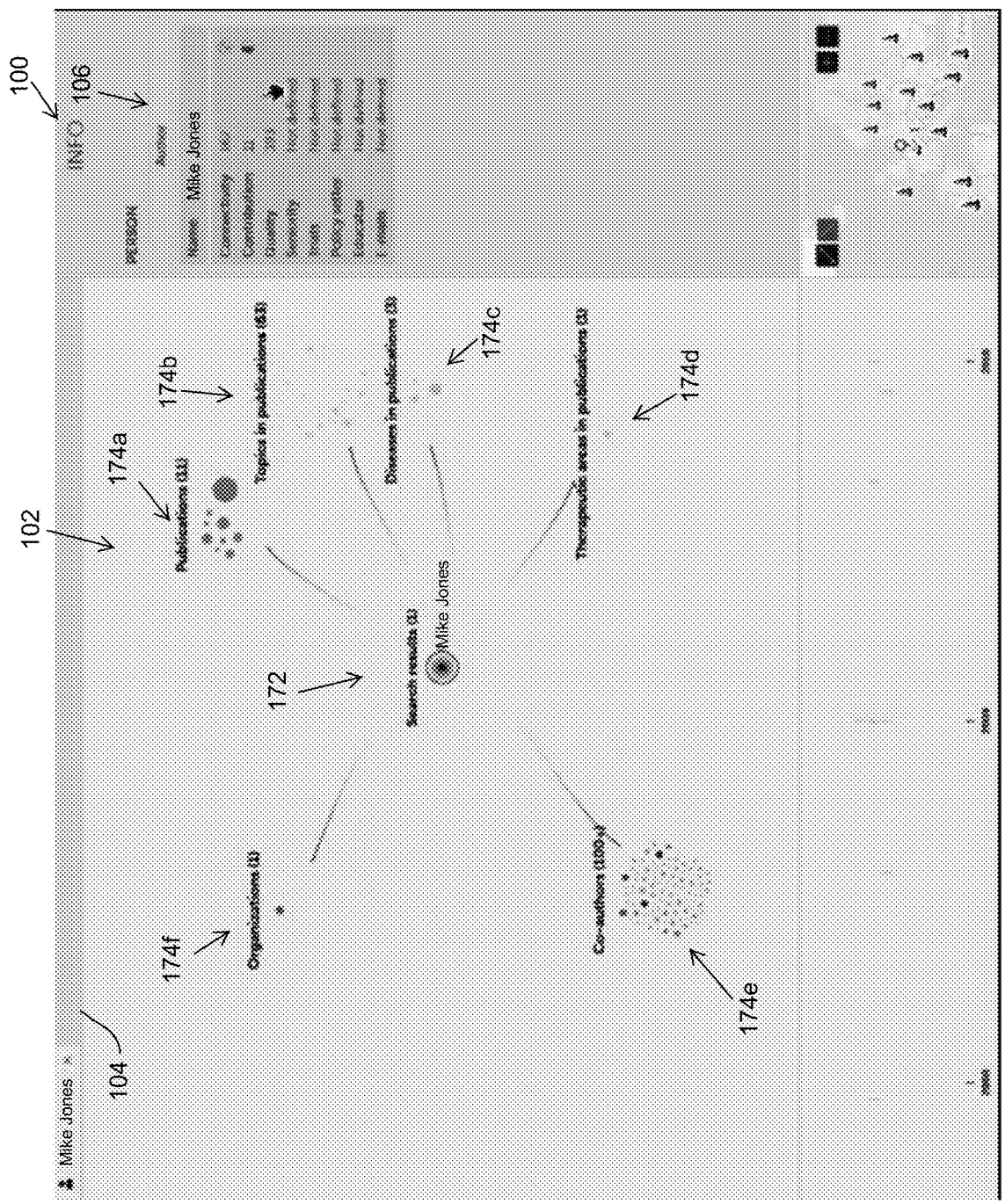

One key advantage of GUI 100 is that it allows a user to explore a professional network by going from one entity to the next to uncover new individual experts and organizations. For example, an individual represented by a center node icon may be linked to a specific organization such as the University of Liege in Belgium in graph database 50. The user may accordingly select the outer node icon representing the organizations generate a list of the organizations in supplemental information section 106. The user then may select the subsection representing University of Liege in supplemental information section 106 to generate a new partial view of the explorable network in graph explorer section 102 with University of Liege being represented by a center node icon 162, as shown in FIG. 14. To investigate individuals linked to the University of Liege, the user can select outer node icon 164a to generate a list of the individuals linked to the University of Liege in supplemental information section 106 as shown in FIG. 15. Upon selection of the subsection 126 of supplemental information section 106 specifically labeled in FIG. 10 related to the individual Mike Jones, exploration application server 42 of computer system 40 accesses graph database 50 and modifies graph explorer section 102 to generate a different partial view of the explorable network on GUI 100, as shown in FIG. 16, with the selected individual, Mike Jones being represented by a center node icon 172 and the different entities linked to Mike Jones in graph database 50 being displayed as selectable outer node icons 174a to 174f. Any of node icons 174a to 174f is selectable to generate the display of a list of the entities represented by the respective node icon 174a to 174f and the corresponding supplemental information in supplement information section 106 as selectable subsections 126, which may be in turn be selected to generate a new graph explore where the selected entity represented by the selected subsection 126 is represented by the center node icon and corresponding entities linked to the selected entity are represented by the outer node icons.

Figure 17:
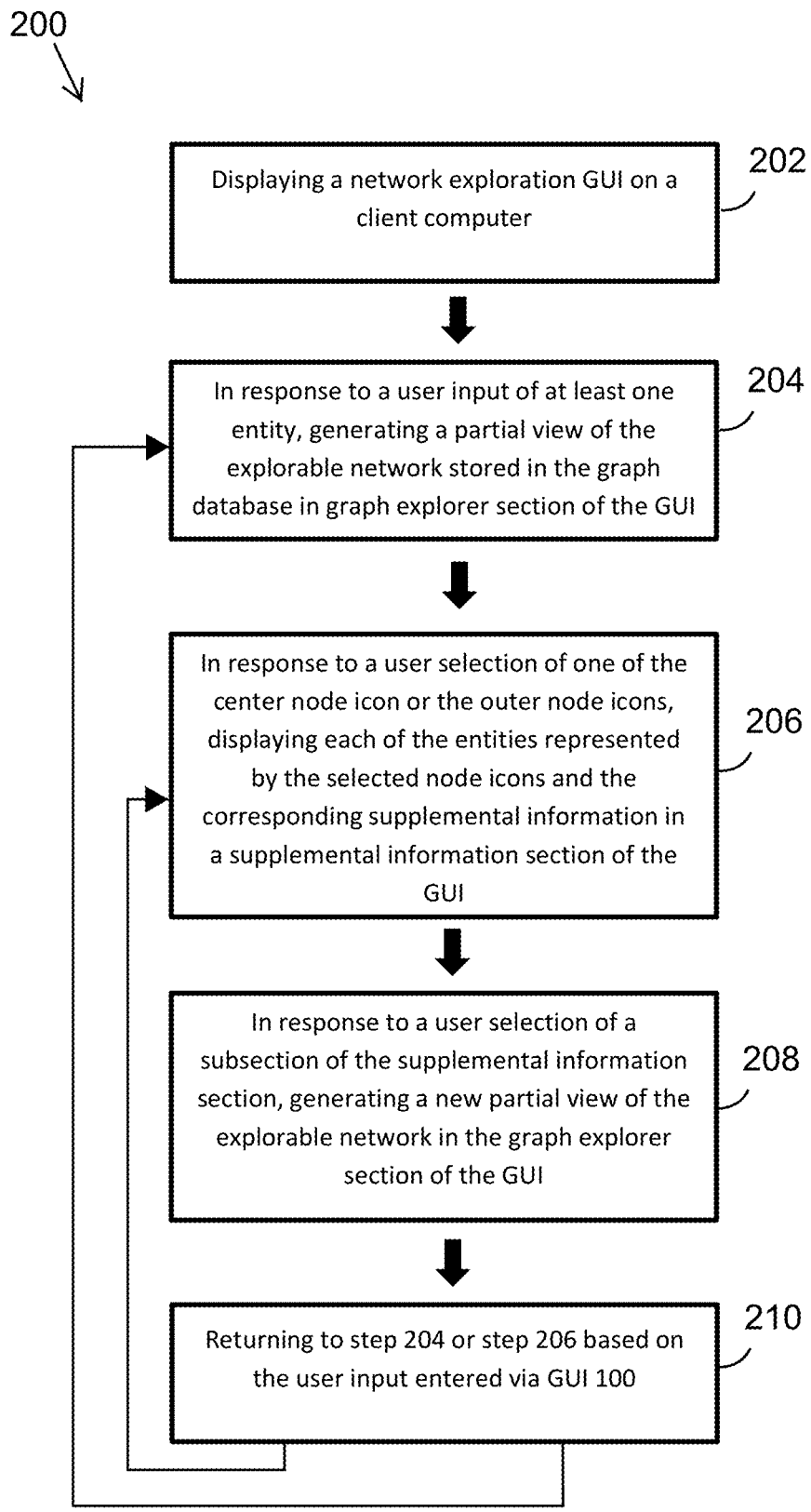
FIG. 17 shows a flow chart representing a method of generating and modifying a network exploration graphical user interface in accordance with an embodiment of the present invention.

FIG. 17 shows a flow chart representing a method 200 of generating and modifying GUI 100 in accordance with an embodiment of the present invention. Method 200 includes a first step 202 of displaying, via computer system 40, GUI 100 on client computer 46.

Next, method 200 includes, a step 204 of generating a partial view of the explorable network stored in graph database 50 in graph explorer section 102. In response to a user input provided to system 40 from client computer 46 via input section 104, network exploration application server 42 generates a partial view of the explorable network stored in graph database 50 in graph explorer section 102. The user input is in the form of at least one entity stored in graph database. The entity may be an individual, an organization, a publication, a clinical trial or a subject area. As similarly noted above, in one preferred embodiment, the individual is an author of a scientific publication and/or an investigator in a clinical trial, the organization is a university, a hospital or a company and the subject area is a topic, disease and/or therapeutic area. The partial view of the explorable network generated in step 204, as shown in the examples of FIGS. 4a to 16, includes a center node icon representing the input entity and a plurality of outer node icons representing entities linked to the input entity in graph database 50. More specifically, in response to the user input provided to system 40 from client computer 46 via input section 104, the JavaScript code running in the client 64 makes a REST call to the frontend application 70. Frontend application 70 consults the enterprise search application 82 to map the user's input to the name of entities in the graph database (again through REST). This information is fed back to the end user via a dropdown list of potential entities or entity groups matching this input. When the user subsequently selects an entity or entity group from this list, this results in an AJAX call to the backend application 74. This checks the database server 88 if this selected entity or entity group has not already been asked before and is therefore cached in this database. If this is the case, the results of this user's query (stored in the database as a JSON document) are returned to the client 64 which enables the client to render the results of the user's query in the different GUI components (102, 106, 108, 110). If the user's query is not cached in the relational database 88, the backend application 74 consults the graph database 50, transforms these results and sends them back to the client 64 which renders the results of the user's query in the different GUI components.

Each of the center node icon and the outer node icons are linked to at least one entity in and supplemental information corresponding to the at least one entity in graph database 50.

Method 200 also includes a step 206 of, in response to a user selection of one of the center node icon or the outer node icons, displaying each of the entities represented by the selected node icon and the corresponding supplemental information in supplemental information section 106. As noted above, each entity is represented by a corresponding selectable subsection 126 within section 106. Each subsection 106 includes the title of the entity and at least one supplemental metric, as generated in network augmentation step 24 of method 10. This supplemental information is loaded together with the information returned to the client in response to user input. Displaying the appropriate supplemental information is dealt with at the client side 64.

In a further step 208 of method 200, in response to a user selection of one of the subsections 126, a new partial view of the explorable network is generated in graph explorer section 102. The new partial view of the explorable network includes a center node icon representing the entity of the selected subsection 126 and a plurality of outer node icons representing further entities linked to the selected entity in graph database 50. Upon selection of a node icon, the client system 64 makes an AJAX call to the backend application 74 via reverse proxy 62. Backend application 74 checks the database server 86 to determine if this selected entity or group of entities has been previously queried and is therefore cached in this database. If this is the case, the results of this user's query, which is stored in database 88 for example as a JSON document, are returned to the client 64 which enables the client to render the results of the user's query in the different sections 102, 106, 108, 110 of GUI 100. If the user's query is not cached in the relational database 88, the backend application 74 consults the graph database 50, transforms these results and sends them back to the client 64, which renders the results of the user's query in the different sections 102, 106, 108, 110 of GUI 100.

After the partial view of the explorable network is generated in graph explorer section 102, a user can generate a different partial view of the explorable network by inputting one or more entities in input section 104, or by selecting any one of the outer node icons for display in supplemental information section 106 and then selected one of the displayed supplemental information subsections 126. The user can also simply review the entities of any entity group directly linked to the input entity and the corresponding supplemental information by selecting any one of the outer node icons for display of the entities represented by the selected node icon and the corresponding supplemental information in section 106. Accordingly, the method includes a step 210 of returning to step 204 or step 206 based on the user input entered via GUI 100, and based on the user inputs, proceeds from step 204 to step 206 to step 208, or from step 206 to step 208. GUI 100 allows a user to repeat these steps for different entities to explore different individuals, organizations, publication information and clinical trial information.

In the preceding specification, the invention has been described with reference to specific exemplary embodiments and examples thereof. It will, however, be evident that various modifications and changes may be made thereto without departing from the broader spirit and scope of invention as set forth in the claims that follow. The specification and drawings are accordingly to be regarded in an illustrative manner rather than a restrictive sense.

What is claimed is:

1. A method of generating an explorable network stored in a graph database in a graphical user interface comprising:
    displaying, by a computer system, the graphical user interface on a client computer;
    accessing, in response to a user input from the client computer in an input section of the graphical user interface, nodes representing entities stored in the graph database and generating a first partial view of the explorable network in a graph explorer section of the graphical user interface, the entities including published scientific works, individuals, organizations and subjects related to published scientific data for the published scientific works, the user input specifying at least one of the entities, the first partial view including a first center node icon representing the at least one user input entity and a plurality of first outer node icons surrounding the first center node icon and each representing other entities linked to the at least one input entity in the graph database;
    displaying, in response to a user selection of the first center node icon or one of the first outer node icons, each of the entities represented by the selected first center or outer node icon and corresponding supplemental information in a respective subsection of a supplemental information section of the graphical user interface that is displayed outside of the graph explorer section, the supplemental information for the individuals being relevant to each individual being a key opinion leader; and
    modifying the graph explorer section, in response to a user selection of one of the subsections of the supplemental information section, to replace the first partial view with a second partial view of the explorable network including a second center node icon representing the entity displayed in the selected subsection and a plurality of second outer node icons surrounding the second center node icon and each representing other entities linked to the entity displayed in the selected subsection in the graph database.

2. The method as recited in claim 1 wherein the published scientific works are represented in the graph database by published works nodes, individuals are represented in the graph database by individual nodes, organizations are represented in the graph database by organization nodes and subjects are represented in the graph database by subject matter nodes.

3. The method as recited in claim 2 wherein each of the individual nodes is directly linked to at least one of the published works nodes in the graph database, with each of the individual nodes being indirectly linked to the subject matter nodes in the graph database via the published works nodes.

4. The method as recited in claim 3 wherein the subject matter nodes include topic nodes representing descriptors, the topic nodes being directly linked to the published works nodes in the graph database.

5. The method as recited in claim 4 wherein the subject matter nodes includes disease nodes representing diseases and therapeutic area nodes representing therapeutic areas, the diseases being a subcategory of the therapeutic areas and the descriptors being a subcategory of the diseases, the therapeutic area nodes being linked to the topic nodes in the graph database via the disease nodes.

6. The method as recited in claim 2 wherein the published scientific works include at least one of results of clinical trials and biomedical scientific publications, the individual nodes being linked to the individual nodes of co-authors of the biomedical scientific publications and co-investigators in the clinical trials via the published works nodes.

7. The method as recited in claim 2 wherein the graph database further includes location nodes representing locations of the organizations, the organization nodes being directly linked to the location nodes, the method further comprising, upon displaying the first partial view, accessing the location nodes directly linked to the organization nodes represented by one of the first center node icon or the first outer node icons, and displaying icons for the locations nodes in a geographic section of the graphical user interface.

8. The method as recited in claim 1 wherein each of the center and outer node icons represent a single node or a cloud including a plurality of nodes of an entity group.

9. The method as recited in claim 1 wherein the supplemental information for each individual in the explorable network is relevant to the individual being a key opinion leader and includes at least three of:
a number of the biomedical scientific publications authored by each individual in the explorable network,
a number of links for each individual in the explorable network with other individual entities in the explorable network based on the biomedical scientific publications,
a number of citations acquired through the biomedical scientific publications for each individual in the explorable network,
a number of the biomedical scientific publications in which each individual in the explorable network was positioned as the last author,
a number of the clinical trials in which each individual in the explorable network participated as an investigator,
a number of reviews in the biomedical scientific publications authored by each person in the explorable network,
a number of guidelines or practice guidelines in the biomedical scientific publications authored by each person in the explorable network, and
an earliest data for a publication in the biomedical scientific publications for each person in the explorable network.

10. The method as recited in claim 1 wherein the first partial view includes a plurality of first links, each of the first links extending outward from the first center node icon to a respective one of the first outer node icons.

11. The method as recited in claim 1 wherein the first center node icon represents a specific individual and the first outer node icons represent a plurality of entities linked to the specific individual in the graph database, the plurality of entities linked to the specific individual in the graph database including published scientific works, individuals, organizations and subjects, and
wherein the displaying, in response to the user selection of the first center node icon or one of the first outer node icons, includes receiving an input of a selection of one of the outer node icons and displaying, in the supplemental information section, a plurality of subsections representing a plurality a further individuals and metrics for each of the further individuals.

12. The method as recited in claim 11 wherein the modifying the graph explorer section, in response to the user selection of one of the subsections of the supplemental information section, includes receiving an input of a selection of one of the subsections representing a selected one of the further individuals and displaying the second center node icon representing the selected further individual and the second outer node icons representing published scientific works, individuals, organizations and subjects linked to the individual in the graph database.

13. The method as recited in claim 12 further comprising displaying, in response to a user selection of one of the second outer node icons representing a plurality of subjects linked to the selected further individual, at least one metric in the supplemental information section for each of the plurality of subjects, each of the at least one metrics being calculated from relationships between the selected further individual represented by the second center node icon and a respective one of the subjects represented by the second outer node icon.

14. The method as recited in claim 12 further comprising displaying, in response to a user selection of the second center node icon, a plurality of metrics in the supplemental information section for the selected further individual, the metrics being calculated from relationships between the selected further individual represented by the second center node icon and at least some of the entities represented by the second outer node icons.

15. The method as recited in claim 1 wherein the first center node icon represents a specific organization and the first outer node icons represent a plurality of entities linked to the specific organization in the graph database, the plurality of entities linked to the specific organization in the graph database including published scientific works, individuals, and subjects, and
wherein the displaying, in response to the user selection of the first center node icon or one of the first outer node icons, includes receiving an input of a selection of one of the outer node icons and displaying, in the supplemental information section, a plurality of subsections representing a plurality of individuals represented by the selected first outer node icon and metrics for each of the individuals.

16. The method as recited in claim 1 wherein the first center node icon represents a plurality of individuals and the first outer node icons represent a plurality of entities linked to the plurality of individuals in the graph database, the plurality of entities linked to the plurality of individuals in the graph database including published scientific works, organizations, and subjects, and
wherein the displaying, in response to the user selection of the first center node icon or one of the first outer node icons, includes receiving an input of a selection of the center outer node icon and displaying, in the supplemental information section, a plurality of subsections representing the plurality of individuals represented by the first center node icon and metrics for each of the further individuals.

17. The method as recited in claim 1 wherein the first center node icon represents a single individual and each of the first outer node icons represents a group of one or entities, each of the groups including a plurality of entities if the group represents more than one entity.

18. A computer system configured for generating an explorable network stored in a graph database in a graphical user interface comprising:
a data structure storing a graph database including data extracted from published scientific data for a plurality of published scientific works and including individual data, organization data and subject matter data identifying entities for each of the published works, the published works including at least one of results of clinical trials and biomedical scientific publications, the entities including the published scientific works, individuals, organizations and subjects, the individual data, organization data and subject matter data being stored in the graph database as an explorable network including a plurality of nodes in which the individuals are represented by individual nodes, the organizations are represented by organization nodes and the subjects are represented by subject matter nodes in the explorable network, each of the individual nodes being linked to at least one of the other individual nodes, at least one of the organization nodes and at least one of the subject matter nodes; and
a processor configured to control the computer system to:
display the graphical user interface on a client computer;
access, in response to a user input from the client computer in an input section of the graphical user interface, the nodes representing entities stored in the graph database and generating a first partial view of the explorable network in a graph explorer section of the graphical user interface, the user input specifying at least one of the entities, the first partial view including a first center node icon representing the at least one user input entity and a plurality of first outer node icons surrounding the first center node icon and each representing other entities linked to the at least one input entity in the graph database;

display, in response to a user selection of the first center node icon or one of the first outer node icons, each of the entities represented by the selected first center or outer node icon and corresponding supplemental information in a respective subsection of a supplemental information section of the graphical user interface that is displayed outside of the graph explorer section, the supplemental information for the individuals being relevant to each individual being a key opinion leader; and modify the graph explorer section, in response to a user selection of one of the subsections of the supplemental information section, to replace the first partial view with a second partial view of the explorable network including a second center node icon representing the entity displayed in the selected subsection and a plurality of second outer node icons surrounding the second center node icon and each representing other entities linked to the entity displayed in the selected subsection in the graph database.

19. The computer system as recited in claim 18 wherein the published scientific works are represented in the graph database by published works nodes, individuals are represented in the graph database by individual nodes, organizations are represented in the graph database by organization nodes and subjects are represented in the graph database by subject matter nodes.

20. The computer system as recited in claim 19 wherein each of the individual nodes is directly linked to at least one of the published works nodes in the graph database, with each of the individual nodes being indirectly linked to the subject matter nodes in the graph database via the published works nodes.

21. The computer system as recited in claim 20 wherein the subject matter nodes include topic nodes representing descriptors, the topic nodes being directly linked to the published works nodes in the graph database.

22. The computer system as recited in claim 21 wherein the subject matter nodes includes disease nodes representing diseases and therapeutic area nodes representing therapeutic areas, the diseases being a subcategory of the therapeutic areas and the descriptors being a subcategory of the diseases, the therapeutic area nodes being linked to the topic nodes in the graph database via the disease nodes.

23. The computer system as recited in claim 19 wherein the published scientific works include at least one of results of clinical trials and biomedical scientific publications, the individual nodes being linked to the individual nodes of co-authors of the biomedical scientific publications and co-investigators in the clinical trials via the published works nodes.

24. The computer system as recited in claim 19 wherein the graph database further includes location nodes representing locations of the organizations, the organization nodes being directly linked to the location nodes, the method further comprising, upon displaying the first partial view, accessing the location nodes directly linked to the organization nodes represented by one of the first center node icon or the first outer node icons, and displaying icons for the locations nodes in a geographic section of the graphical user interface.

25. The computer system as recited in claim 18 wherein each of the center and outer node icons represent a single node or a cloud including a plurality of nodes of an entity group.

26. The computer system as recited in claim 18 wherein the supplemental information for each individual in the explorable network is relevant to the individual being a key opinion leader and includes at least three of:

a number of the biomedical scientific publications authored by each individual in the explorable network, a number of links for each individual in the explorable network with other individual entities in the explorable network based on the biomedical scientific publications, a number of citations acquired through the biomedical scientific publications for each individual in the explorable network, a number of the biomedical scientific publications in which each individual in the explorable network was positioned as the last author, a number of the clinical trials in which each individual in the explorable network participated as an investigator, a number of reviews in the biomedical scientific publications authored by each person in the explorable network, a number of guidelines or practice guidelines in the biomedical scientific publications authored by each person in the explorable network, and an earliest data for a publication in the biomedical scientific publications for each person in the explorable network.

* * * * *